(12) United States Patent
Schroth et al.

(10) Patent No.: US 6,420,109 B1
(45) Date of Patent: Jul. 16, 2002

(54) NUCLEIC ACID LIGAND INTERACTION ASSAYS

(75) Inventors: Gary P. Schroth, Foster City; Thomas Wayne Bruice, Carlsbad; Young J. Suh, Union City, all of CA (US)

(73) Assignee: Genelabs Technologies, Inc., Redwood City, CA (US)

( * ) Notice: Subject to any disclaimer, the term of this patent is extended or adjusted under 35 U.S.C. 154(b) by 0 days.

(21) Appl. No.: 09/151,890

(22) Filed: Sep. 11, 1998

(51) Int. Cl.$^7$ .................................................. C12Q 1/68
(52) U.S. Cl. .......................................... 435/6; 436/501
(58) Field of Search ...................... 435/6, 810; 436/501; 935/77, 78

(56) References Cited

U.S. PATENT DOCUMENTS

| | | | |
|---|---|---|---|
| 4,382,074 A | | 5/1983 | Hart ............................. 436/537 |
| 4,820,630 A | * | 4/1989 | Taub .............................. 435/5 |
| 5,593,834 A | * | 1/1997 | Lane et al. ...................... 435/6 |
| 5,747,254 A | * | 5/1998 | Pontius .......................... 435/6 |
| 5,853,986 A | * | 12/1998 | Petrie, III et al. ............... 435/6 |

FOREIGN PATENT DOCUMENTS

| | | |
|---|---|---|
| WO | WO 95/00666 | 1/1995 |
| WO | WO 97/09342 | 3/1997 |
| WO | WO 98/10096 | 3/1998 |
| WO | 99/63117 | * 12/1999 |

OTHER PUBLICATIONS

Cardullo et al., Proc. Nat'l Acad Sci (USA), vol. 85, No. 23, pp. 8790–8794, 1988.*
Matthews et al., Analytical Biochem., vol. 169, pp. 1–25, 1988.*
Chen, Qi, et al. "Structure–Based Discovery of Ligands Targeted to the RNA Double Helix," Biochemistry 36: 11402–110407 (1997).
Diebold, R.J. et al. "Molecular basis of cooperative DNA bending and oriented heterodimer binding in the NFAT1–Fos–Jun ARRE2 complex," Proc. Natl. Acad. Sci. USA 95(14):7915–20 (1998).
Wilson, David W., et al., "Evaluation of Drug–Nucleic Acid Interactions by Thermal Melting Curves," *Methods of Molecular Biology, vol. 90:Drug–DNA Interaction Protocols,* K.R. Fox (ed.), Humana Press Inc., Totowa, NJ, pp. 219–231.

* cited by examiner

Primary Examiner—Ardin H. Marschel
(74) Attorney, Agent, or Firm—LeeAnn Gorthey

(57) ABSTRACT

Methods for determining the relative binding affinities of various ligands to various nucleic acid sequences are described. In a direct binding assay, the effect of adding increasing amounts of a ligand on a signal generated by two "indicator" oligonucleotides is observed. Also described is a competitive binding assay, in which a competitor oligonucleotide is added to an indicator duplex having a ligand bound thereto. The assays allow the rapid and convenient determination of nucleic acid binding specificities and base pair determinants of specificity of particular ligands.

28 Claims, 16 Drawing Sheets

Single Stranded Nucleic Acid        Duplex Nucleic Acid        Drug Bound Nucleic Acid

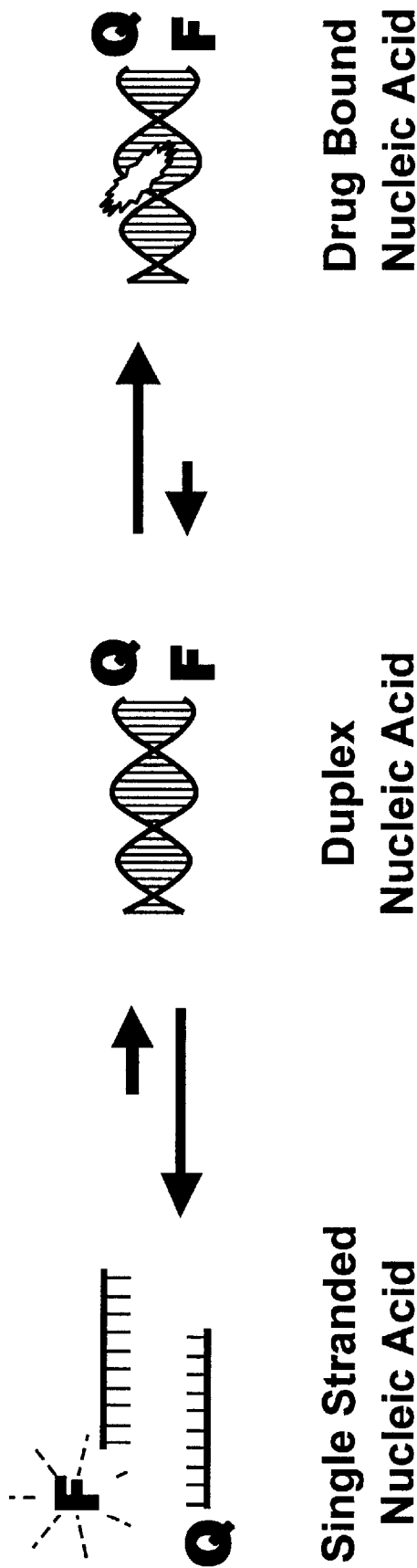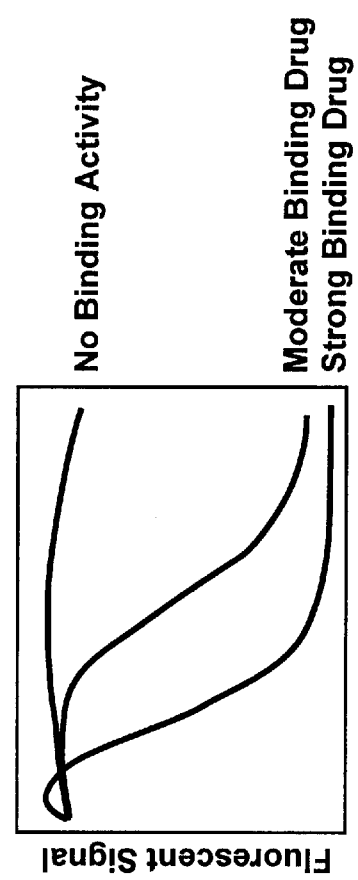
Fig. 1A
Fig. 1B

SEQUENCE LISTING

```
<160> NUMBER OF SEQ ID NOS:  80

<210> SEQ ID NO 1
<211> LENGTH: 10
<212> TYPE: DNA
<213> ORGANISM: Artificial Sequence
<220> FEATURE:
<221> NAME/KEY: misc_binding
<222> LOCATION: (1)...(10)
<223> OTHER INFORMATION: Synthesized test oligonucleotide for binding
      studies

<400> SEQUENCE: 1
cttttttttt                                                              10

<210> SEQ ID NO 2
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 2
ctttattatt tt                                                           12

<210> SEQ ID NO 3
<211> LENGTH: 9
<212> TYPE: DNA
<213> ORGANISM: Artificial Sequence
<220> FEATURE:
<221> NAME/KEY: misc_binding
<222> LOCATION: (1)...(9)
<223> OTHER INFORMATION: synthesized test oligonucleotide for binding
      studies

<400> SEQUENCE: 3 ctctctctc                                                                9

<210> SEQ ID NO 4
<211> LENGTH: 10
```

```
<212> TYPE: DNA
<213> ORGANISM: Artificial Sequence
<220> FEATURE:
<221> NAME/KEY: modified_base
<222> LOCATION: (3)...(4)
<223> OTHER INFORMATION: I
<221> NAME/KEY: modified_base
<222> LOCATION: (7)...(8)
<223> OTHER INFORMATION: I
<221> NAME/KEY: misc_binding
<222> LOCATION: (1)...(10)
<223> OTHER INFORMATION: synthesized test oligonucleotide for binding
      studies

<400> SEQUENCE: 4 ccnnccnncc                                                          10

<210> SEQ ID NO 5
<211> LENGTH: 10
<212> TYPE: DNA
<213> ORGANISM: Artificial Sequence
<220> FEATURE:
<221> NAME/KEY: modified_base
<222> LOCATION: (5)...(6)
<223> OTHER INFORMATION: I
<221> NAME/KEY: misc_binding
<222> LOCATION: (1)...(10)
<223> OTHER INFORMATION: synthesized oligonucleotide for ligand binding
      studies

<400> SEQUENCE: 5 ggccnnccgg                                                          10

<210> SEQ ID NO 6
<211> LENGTH: 7
<212> TYPE: DNA
<213> ORGANISM: Artificial Sequence
<220> FEATURE:
<221> NAME/KEY: misc_binding
<222> LOCATION: (1)...(7)
<223> OTHER INFORMATION: synthesized test oligonucleotide for ligand
      studies

<400> SEQUENCE: 6 ccgcgcc                                                              7

<210> SEQ ID NO 7
<211> LENGTH: 6
<212> TYPE: DNA
<213> ORGANISM: Artificial Sequence
<220> FEATURE:
<221> NAME/KEY: misc_binding
<222> LOCATION: (1)...(6)
<223> OTHER INFORMATION: synthesized test oligonucleotide for binding
      studies

<400> SEQUENCE: 7 cgcgcg                                                               6

<210> SEQ ID NO 8
<211> LENGTH: 7
<212> TYPE: DNA
<213> ORGANISM: Artificial Sequence
<220> FEATURE:
<221> NAME/KEY: misc_binding
<222> LOCATION: (1)...(7)
<223> OTHER INFORMATION: synthesized test oligonucleotide for binding
      studies

<400> SEQUENCE: 8
```

```
cccccc                                                                    7

<210> SEQ ID NO 9
<211> LENGTH: 11
<212> TYPE: DNA
<213> ORGANISM: Artificial Sequence
<220> FEATURE:
<221> NAME/KEY: misc_binding
<222> LOCATION: (1)...(11)
<223> OTHER INFORMATION: synthesized test oligonucleotide for binding
      studies

<400> SEQUENCE: 9
gatatatata g                                                              11

<210> SEQ ID NO 10
<211> LENGTH: 8
<212> TYPE: DNA
<213> ORGANISM: Artificial Sequence
<220> FEATURE:
<221> NAME/KEY: misc_binding
<222> LOCATION: (1)...(8)
<223> OTHER INFORMATION: synthesized test oligonucleotide for binding
      studies

<400> SEQUENCE: 10 ggtattcg                                                                  8

<210> SEQ ID NO 11
<211> LENGTH: 8
<212> TYPE: DNA
<213> ORGANISM: Artificial Sequence
<220> FEATURE:
<221> NAME/KEY: misc_binding
<222> LOCATION: (1)...(8)
<223> OTHER INFORMATION: synthesized test oligonucleotide for binding
      studies

<400> SEQUENCE: 11 gcgtattt                                                                  8

<210> SEQ ID NO 12
<211> LENGTH: 9
<212> TYPE: DNA
<213> ORGANISM: Artificial Sequence
<220> FEATURE:
<221> NAME/KEY: misc_binding
<222> LOCATION: (1)...(9)
<223> OTHER INFORMATION: synthesized test oligonucleotide for binding
      studies

<400> SEQUENCE: 12 gcggtattt                                                                 9

<210> SEQ ID NO 13
<211> LENGTH: 6
<212> TYPE: DNA
<213> ORGANISM: Artificial Sequence
<220> FEATURE:
<221> NAME/KEY: misc_signal
<222> LOCATION: (1)...(6)
<223> OTHER INFORMATION: synthesized test oligonucleotide for binding
      studies.

<400> SEQUENCE: 13 cgcgcc                                                                    6

<210> SEQ ID NO 14
```

```
<211> LENGTH: 14
<212> TYPE: RNA
<213> ORGANISM: Artificial Sequence
<220> FEATURE:
<221> NAME/KEY: misc_binding
<222> LOCATION: (1)...(14)
<223> OTHER INFORMATION: synthesized test oligonucleotide for binding
      studies

<400> SEQUENCE: 14
caugaucuga acuu                                                           14

<210> SEQ ID NO 15
<211> LENGTH: 14
<212> TYPE: RNA
<213> ORGANISM: Artificial Sequence
<220> FEATURE:
<221> NAME/KEY: misc_binding
<222> LOCATION: (1)...(14)
<223> OTHER INFORMATION: synthesized test oligonucleotide for bindng
      studies

<400> SEQUENCE: 15
aaguucagau cuag                                                           14

<210> SEQ ID NO 16
<211> LENGTH: 12
<212> TYPE: RNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 16
guucagaucu ag                                                             12

<210> SEQ ID NO 17
<211> LENGTH: 10
<212> TYPE: RNA
<213> ORGANISM: Artificial Sequence
<220> FEATURE:
<221> NAME/KEY: misc_binding
<222> LOCATION: (1)...(10)
<223> OTHER INFORMATION: synthesized test oligonucleotide for binding
      studies

<400> SEQUENCE: 17
ucagaucuag                                                                10

<210> SEQ ID NO 18
<211> LENGTH: 9
<212> TYPE: RNA
<213> ORGANISM: Artificial Sequence
<220> FEATURE:
<221> NAME/KEY: misc_binding
<222> LOCATION: (1)...(9)
<223> OTHER INFORMATION: synthesized test oligonucleotide for binding
      studies

<400> SEQUENCE: 18 cagaucuag                                                                  9

<210> SEQ ID NO 19
<211> LENGTH: 14
<212> TYPE: DNA
<213> ORGANISM: Artificial Sequence
<220> FEATURE:
```

```
<221> NAME/KEY: misc_binding
<222> LOCATION: (1)...(14)
<223> OTHER INFORMATION: synthesized test oligonucleotide for binding
      studies

<400> SEQUENCE: 19
ctagatctga actt                                                     14

<210> SEQ ID NO 20
<211> LENGTH: 14
<212> TYPE: DNA
<213> ORGANISM: Artificial Sequence
<220> FEATURE:
<221> NAME/KEY: misc_binding
<222> LOCATION: (1)...(14)
<223> OTHER INFORMATION: synthesized test oligonucleotide for binding
      studies

<400> SEQUENCE: 20
aagttcagat ctag                                                     14

<210> SEQ ID NO 21
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 21
gttcagatct ag                                                       12

<210> SEQ ID NO 22
<211> LENGTH: 10
<212> TYPE: DNA
<213> ORGANISM: Artificial Sequence
<220> FEATURE:
<221> NAME/KEY: misc_binding
<222> LOCATION: (1)...(10)
<223> OTHER INFORMATION: synthesized test oligonucleotide for binding
      studies

<400> SEQUENCE: 22
tcagatctag                                                          10

<210> SEQ ID NO 23
<211> LENGTH: 10
<212> TYPE: RNA
<213> ORGANISM: Artificial Sequence
<220> FEATURE:
<221> NAME/KEY: misc_binding
<222> LOCATION: (1)...(10)
<223> OTHER INFORMATION: synthesized test oligonucleotide for binding
      studies

<400> SEQUENCE: 23
cuagaucuga                                                          10

<210> SEQ ID NO 24
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies
```

```
<400> SEQUENCE: 24
ctagatctga ac                                                              12

<210> SEQ ID NO 25
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 25
cccggccggc cc                                                              12

<210> SEQ ID NO 26
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 26
cccggacggc cc                                                              12

<210> SEQ ID NO 27
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 27
cccggaaccg cc                                                              12

<210> SEQ ID NO 28
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 28
cccggtaccg cc                                                              12

<210> SEQ ID NO 29
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 29
cccgaaaccg cc                                                              12
```

<210> SEQ ID NO 30
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binidng
      studies

<400> SEQUENCE: 30
cccgataccg cc                                                            12

<210> SEQ ID NO 31
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 31
cccgaaaacg cc                                                            12

<210> SEQ ID NO 32
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 32
cccgatatcg cc                                                            12

<210> SEQ ID NO 33
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 33
cccaaaaagg cc                                                            12

<210> SEQ ID NO 34
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 34
ccctatatcg cc                                                            12

<210> SEQ ID NO 35
<211> LENGTH: 12

```
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 35
cccaaaaaag cc                                                        12

<210> SEQ ID NO 36
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 36
ccctatatag cc                                                        12

<210> SEQ ID NO 37
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 37
ccaaaaaaag cc                                                        12

<210> SEQ ID NO 38
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 38
ccatatatag cc                                                        12

<210> SEQ ID NO 39
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 39
ccaaaaaaaa cc                                                        12

<210> SEQ ID NO 40
<211> LENGTH: 12
<212> TYPE: DNA
<213> ORGANISM: Artificial Sequence
<220> FEATURE:
<221> NAME/KEY: misc_binding
```

```
<222> LOCATION: (1)...(12)
<223> OTHER INFORMATION: synthesized test oligonucleotide for binding
      studies

<400> SEQUENCE: 40
ccatatatat cc                                                              12

<210> SEQ ID NO 41
<211> LENGTH: 13
<212> TYPE: DNA
<213> ORGANISM: Artificial Sequence
<220> FEATURE:
<221> NAME/KEY: misc_binding
<222> LOCATION: (1)...(13)
<223> OTHER INFORMATION: synthesized test oligonucleotide for binding
      studies

<400> SEQUENCE: 41
gtgtgtgtgt gtg                                                             13

<210> SEQ ID NO 42
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 42
cccggccggc cc                                                              12

<210> SEQ ID NO 43
<211> LENGTH: 13
<212> TYPE: DNA
<213> ORGANISM: Artificial Sequence
<220> FEATURE:
<221> NAME/KEY: misc_binding
<222> LOCATION: (1)...(13)
<223> OTHER INFORMATION: synthesized test oligonucletoide for binding
      studies

<400> SEQUENCE: 43
ctctctctct ctc                                                             13

<210> SEQ ID NO 44
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 44
catgtcagtc ga                                                              12

<210> SEQ ID NO 45
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonuclotide for binding
      studies
```

-continued

<400> SEQUENCE: 45
ggaaggaagg aa                                                              12

<210> SEQ ID NO 46
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 46
cccgaaaacg cc                                                              12

<210> SEQ ID NO 47
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 47
cccgaattcg cc                                                              12

<210> SEQ ID NO 48
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 48
cccgtatacg cc                                                              12

<210> SEQ ID NO 49
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 49
cccgatatcg cc                                                              12

<210> SEQ ID NO 50
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 50
cccgttaacg cc                                                              12

```
<210> SEQ ID NO 51
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucletoide for binding
      studies

<400> SEQUENCE: 51
cccgtgttcg cc                                                           12

<210> SEQ ID NO 52
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 52
cccgaaaaac cg                                                           12

<210> SEQ ID NO 53
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 53
cccgaaattc cg                                                           12

<210> SEQ ID NO 54
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 54
cccgatatac cg                                                           12

<210> SEQ ID NO 55
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 55
cccgaataac cg                                                           12

<210> SEQ ID NO 56
<211> LENGTH: 12
<212> TYPE: DNA
```

-continued

```
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 56
cccgtaaatc cg                                                              12

<210> SEQ ID NO 57
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 57
cccgataaac cg                                                              12

<210> SEQ ID NO 58
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 58
cccgttaaac cg                                                              12

<210> SEQ ID NO 59
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 59
cccgattaac cg                                                              12

<210> SEQ ID NO 60
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 60
cccgaattac cg                                                              12

<210> SEQ ID NO 61
<211> LENGTH: 12
<212> TYPE: DNA
<213> ORGANISM: Artificial Sequence
<220> FEATURE:
<221> NAME/KEY: misc_binding
<222> LOCATION: (1)...(12)
```

```
<223> OTHER INFORMATION: synthesized test oligonucleotide for binding
      studies

<400> SEQUENCE: 61
cccgtaaaac cg                                                              12

<210> SEQ ID NO 62
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 62
cccgaaaatc cg                                                              12

<210> SEQ ID NO 63
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 63
cccgataaac cg                                                              12

<210> SEQ ID NO 64
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 64
ccccaattcg cc                                                              12

<210> SEQ ID NO 65
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 65
ccccaattag cc                                                              12

<210> SEQ ID NO 66
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 66
```

```
cccaaattgg cc                                                    12

<210> SEQ ID NO 67
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 67
ccccaattgg cc                                                    12

<210> SEQ ID NO 68
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 68
cccaaattcg cc                                                    12

<210> SEQ ID NO 69
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 69
cccaaattag cc                                                    12

<210> SEQ ID NO 70
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 70
cccaaatttg cc                                                    12

<210> SEQ ID NO 71
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 71
cccgaattag cc                                                    12
```

```
<210> SEQ ID NO 72
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 72
ccctaattag cc                                                             12

<210> SEQ ID NO 73
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 73
cccgaattcg cc                                                             12

<210> SEQ ID NO 74
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 74
ccgttgtttc cg                                                             12

<210> SEQ ID NO 75
<211> LENGTH: 28
<212> TYPE: DNA
<213> ORGANISM: Artificial Sequence
<220> FEATURE:
<221> NAME/KEY: misc_binding
<222> LOCATION: (1)...(28)
<223> OTHER INFORMATION: synthesized test oligonucleotide for binding
      studies

<400> SEQUENCE: 75
caacgatagc cgatgttagg cagctcac                                            28

<210> SEQ ID NO 76
<211> LENGTH: 21
<212> TYPE: DNA
<213> ORGANISM: Artificial Sequence
<220> FEATURE:
<221> NAME/KEY: misc_binding
<222> LOCATION: (1)...(21)
<223> OTHER INFORMATION: synthesized test oligonucleotide for binding
      studies

<400> SEQUENCE: 76
gcctaacatc ggctatcgtt g                                                   21

<210> SEQ ID NO 77
<211> LENGTH: 28
<212> TYPE: DNA
<213> ORGANISM: Artificial Sequence
```

-continued

```
<220> FEATURE:
<221> NAME/KEY: misc_binding
<222> LOCATION: (1)...(28)
<223> OTHER INFORMATION: synthesized test oligonucletoide for binding
      studies

<400> SEQUENCE: 77
gtgagctgcc taacatcggc tatcgttg                                       28

<210> SEQ ID NO 78
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 78
caaaaatttt tc                                                        12

<210> SEQ ID NO 79
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 79
cccgcgcgcg cc                                                        12

<210> SEQ ID NO 80
<211> LENGTH: 12
<212> TYPE: DNA
<213> ORGANISM: Artificial Sequence
<220> FEATURE:
<223> OTHER INFORMATION: oligonucleotide
<221> NAME/KEY: misc_feature
<222> LOCATION: (4)...(4)
<223> OTHER INFORMATION: n=a, t, c, or g
<221> NAME/KEY: misc_feature
<222> LOCATION: (9)...(9)
<223> OTHER INFORMATION: n=a, t, c, or g

<400> SEQUENCE: 80
cccnaattng cc                                                        12
```

NUCLEIC ACID LIGAND INTERACTION ASSAYS

FIELD OF THE INVENTION

The invention is directed to the determination of relative binding affinities of various ligands to various nucleic acid sequences, and in particular to the determination of binding specificities and base pair determinants of specificity of particular ligands via a competitive binding assay.

REFERENCES

Brophy, G. P. et al., U.S. Pat. No. 5,789,179 (1998).
Campbell, A. K., *Chemiluminescence: Principles and Applications in Biology and Medicine;* VCH, Ellis Horwood Ltd.: New York, 1988.
Cook, N. D., U.S. Pat. No. 5,665,562 (1997).
Haugland, R. P. (1996) *Handbook of Fluorescent Probes and Research Chemicals* (Spenze, M. T. Z., ed.) Molecular Probes, Eugene, Oreg.
Nieman, T., "Chemiluminescence: Techniques, Liquid-Phase Chemiluminescence", in *Encyclopedia of Analytical Science,* pp 613–621; Academic Press: Orlando, Fla., 1995.
Cantor, C. R., "Lighting Up Hybridization", *Nature Biotechnology* 14:264 (1996).
Chen, Q., Shafer, R. H., and Kuntz, I. D., *Biochemistry* 36:11402–7 (1997).
Hart, H., U.S. Pat. No. 4,271,139 (1978) and U.S. Pat. No. 4,382,074 (1983).
Morrison, L. E. and Stols, L. M., "Sensitive Fluorescence-Based Thermodynamic and Kinetic Measurements of DNA Hybridization in Solution", *Biochemistry* 32: 3095–3104 (1993).
Morrison, L. E., Halder, T. C., and Stols, L. M., "Solution Phase Detection of Polynucleotides Using Interacting Fluorescent Labels and Competitive Hybridization", *Anal. Biochem.* 183:231–244 (1989).
Saenger, W., in *Principles of Nucleic Acid Structure* (Cantor, C. R., ed.), Springer-Verlag, New York, 1984.
Tyagi, S. and Kramer, F. R., "Molecular Beacons: Probes that Fluoresce upon Hybridization", *Nature Biotech.* 14:303–306 (1996).
Tyagi, S., Bratu, D. P., and Kramer, F. R., "Multicolor Molecular Beacons for Allele Discrimination", *Nature Biotech.* 16:49–53 (1998).
Wilson, W. D., Tanious, F. A., Fernandez-Saiz, M., and Rigl, C. T., "Evaluation of Drug-Nucleic Acid Interactions by Thermal Melting Curves" in *Methods in Molecular Biology, Vol. 90: Drug-DNA Interaction Protocols* (Fox, K. R. ed.), Humana Press, Totawa, N.J. pp. 219–240.

BACKGROUND OF THE INVENTION

The specific molecular recognition of nucleic acids is fundamental to essential processes in molecular biology, including replication, transcription and translation. It has been shown that, in the majority of cases, binding of ligands to double-stranded nucleic acids stabilizes the duplex, or helical, form of DNA or RNA. (See, for example, Wilson et al.) The current understanding of the interactions between DNA or RNA and bound ligands is largely based on information obtained via biochemical and biophysical methods such as chemical and nuclease footprinting, affinity probing, UV, CD, fluorescent, and NMR spectroscopy, calorimetry, gel electrophoresis, and x-ray crystallography.

In a typical application of DNA footprinting, for example, a labeled oligonucleotide is digested with a DNA nuclease to the extent necessary to create an average of one cut per chain, producing a series of fragments differing by one base pair in length. A similar operation is performed on the oligonucleotide having a bound ligand. The ligand protects the oligonucleotide, at and around its binding site, from nuclease activity, creating a characteristic pattern of "missing" fragments at this site on a polyacrylamide gel following electrophoresis. This method suffers from the disadvantages of being very time and labor intensive, and in revealing not necessarily the critical molecular determinants for the ligand binding, but rather the area of the oligonucleotide that is shielded by the bulk of the ligand.

The most widely used method for studying nucleic acid hybridization is thermal denaturation, or melting, of duplex nucleic acids. Ligand binding has also been studied using thermal denaturation, since binding of ligands to duplex DNA or RNA tends to stabilize the helix against melting. Techniques used to observe this change include UV, fluorescent, CD and NMR spectroscopy, electrophoresis, and calorimetry.

Certain disadvantages are inherent in ligand binding studies based on observation of duplex denaturation, or melting. The methods provide information about binding only at or near the $T_m$ of the system, rather than at standard (25° C.) or physiological (37° C.) temperatures. Because the presence of the ligand generally raises the $T_m$ of the duplex, it is necessary that the ligand, e.g. the drug, be stable at this higher temperature. In addition, these methods do not routinely provide information about the binding site of the ligand (see, for example, Chen et al., 1997; Wilson et al., 1997). Therefore, the need exists for assays which are sensitive, are rapidly and simply carried out, and provide precise binding site information.

SUMMARY OF THE INVENTION

In one aspect, the invention provides a method of determining the binding affinity of a ligand to an oligonucleotide sequence. The ligand may be any of a wide range of nucleic acid binding groups, including a metal ion, a small organic molecule, a protein, a multi-protein complex, or a polynucleotide. According to the method, a mixture is formed of first and second oligonucleotides. The first oligonucleotide comprises a first group which is effective to produce a detectable signal, and the second oligonucleotide, which is effective to hybridize with the first oligonucleotide by Watson-Crick base pairing, comprises a second group which is effective to detectably alter the signal when the first and second oligonucleotides hybridize to form a duplex. In accordance with a preferred embodiment, the mixture is formed under conditions such that, in the absence of the ligand, the two oligonucleotides exist primarily in single-stranded form. The detectable signal, or lack thereof, is then observed in the absence of the ligand and in the presence of the ligand. Preferably, the ligand is added in increasing concentrations, with the mixture held at a substantially constant temperature, which may be at or near room temperature, during the addition. By titrating in the ligand and observing the change in signal, apparent $K_d$ can be determined for any oligonucleotide sequence.

In various embodiments of the first and second groups, the second group is effective to stimulate or magnify the signal, to reduce or quench the signal, or to otherwise modify the signal upon hybridization of the first and second oligonucleotides. For example, where the signal is emitted radiation, e.g. from a fluorescent dye, the second group may be effective to quench the radiation, or to alter the wavelength of the radiation, by absorption and reemission, upon hybridization. In another embodiment, the first group is a radioactive emitting group, and the second group comprises a scintillant. Alternatively, the first group or the second group is a chemiluminescent group.

In one embodiment, the first group is attached at the 5'-end or 3'-end of the first oligonucleotide, and the second group is attached at the 3'-end or 5'-end, respectively, of the second oligonucleotide. Alternatively, the first and second groups can be attached at any position within the oligonucleotide.

In another aspect, the invention provides a related method of determining the binding affinity of a ligand to an oligonucleotide sequence. In accordance with this method, a duplex is formed of a first oligonucleotide, comprising a first group effective to produce a detectable signal, and a second oligonucleotide, effective to hybridize with the first oligonucleotide by Watson-Crick base pairing, and comprising a second group effective to detectably alter the signal when the first and second oligonucleotides hybridize. In this method, the first and second oligonucleotides differ in length, such that the resulting duplex has an overhang region, preferably about 4–7 nucleotides in length. An unlabeled displacement strand, which is effective to displace one of the oligonucleotides from the duplex in the absence of the ligand, is then added. The effect of this addition on the signal is observed in the absence and in the presence of the ligand. In a preferred embodiment, the forming, adding and observing steps are carried out at a substantially constant temperature, which may be at or near room temperature.

This method may further include the steps of adding a competitor oligonucleotide and observing the effect of such addition on the signal. The competitor oligonucleotide may be a duplex DNA, duplex RNA, duplex DNA/RNA hybrid, or a single stranded oligonucleotide.

In a further embodiment, the invention provides a method of determining the relative binding affinities of a ligand to different oligonucleotide sequences. The ligand may be, for example, a metal ion, a small organic or inorganic molecule, a protein, a multi-protein complex, or a polynucleotide. Accordingly, there is provided a mixture of a first oligonucleotide, which comprises a first group effective to emit a detectable signal, and a second oligonucleotide, effective to hybridize with the first sequence by Watson-Crick base pairing, which comprises a second group effective to detectably alter the signal when the first and second oligonucleotides hybridize. An indicator duplex of the two oligonucleotides, having the ligand bound thereto, is formed. A competitor oligonucleotide is then added, and the effect of this addition on the signal is observed. The competitor oligonucleotide is generally unlabeled, and may be a duplex DNA, duplex RNA, duplex DNA/RNA hybrid, or a single stranded oligonucleotide.

In a preferred embodiment, the indicator duplex is formed under conditions such that, in the absence of the ligand, the first and second oligonucleotides would exist primarily in single-stranded form. Preferably, the adding and observing steps are carried out at a substantially constant temperature, which may be at or near room temperature.

As above, the first group is preferably attached at the 5'-end or 3'-end of the first oligonucleotide, and the second group at the 3'-end or 5'-end, respectively, of the second oligonucleotide. In various embodiments, the first and second groups are, respectively, a radioactive emitting group and a scintillant, groups effective to produce a chemiluminescent reaction, or a fluorescent group and a group effective to absorb radiation emitted by the fluorescent group.

BRIEF DESCRIPTION OF THE DRAWINGS

FIG. 1A is a schematic illustrating the equilibrium between single stranded and duplex nucleic acids, and the shift towards the duplex form upon ligand binding, in a direct assay;

FIG. 1B illustrates the effect of increasing drug concentration on the fluorescent signal, for an assay as illustrated in FIG. 1A, for drugs having different binding affinities;

DETAILED DESCRIPTION OF THE INVENTION

I. Definitions

Figure 2A:
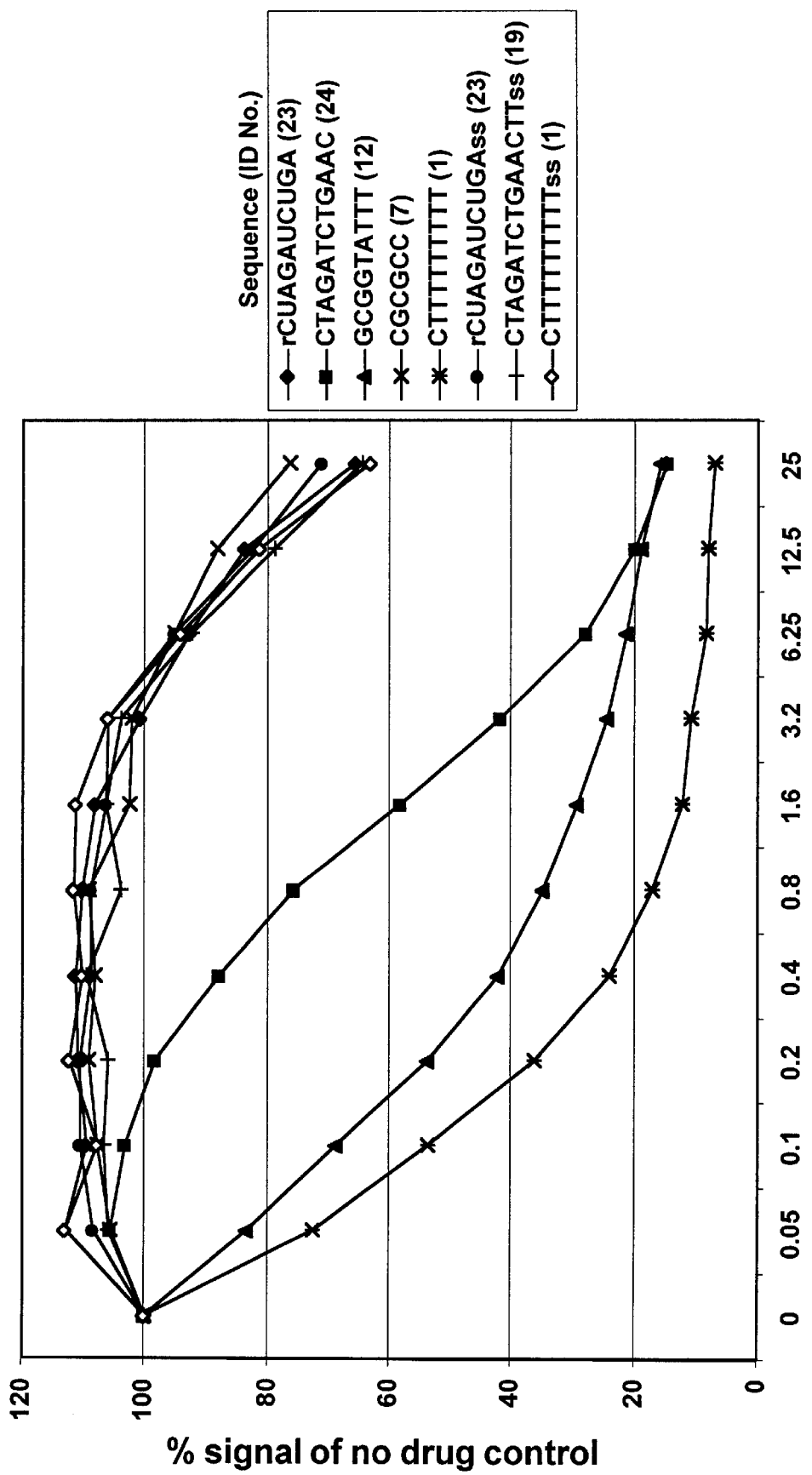
FIGS. 2A–2C show the decrease in fluorescence accompanying an increase in hybridization for a series of different-sequence DNA and RNA oligomers, in the presence of increasing amounts of netropsin (2A), bekanomycin (2B), and actinomycin D (2C)

A "ligand" refers to any molecule or species which binds nucleic acids. Ligands may include a single metal ion (e.g. $Li^+$, $Na^+$, $Mg^{+2}$, etc.), small molecule organic or inorganic compounds (e.g. polyamines, polyamides, polypeptides, or drugs), proteins, multi-protein complexes, or polynucleotides.

Two sequences which are "complementary" are able to form a duplex by exact one-to-one Watson-Crick base pairing between the bases in the two sequences, where adenine (A) base pairs with thymine (T), or uracil (U) in RNA, and cytosine (C) base pairs with guanine (G). Inosine (I) can base pair with cytosine, adenine, or uracil. A sequence which is complementary to a given sequence is referred to as its complement.

An "indicator pair" refers to first and second oligonucleotides, effective to form a duplex ("indicator duplex") by hybridization, where the first oligo has, typically at its 5' end, a group effective to produce a detectable signal, and the second oligo has, typically at its 3' end, a group effective to detectably alter this signal when the oligonucleotides form such a duplex. The first and second oligonucleotides are generally complementary.

II. Ligand-Nucleic Acid Binding Assays

A. Direct Assay

In a direct binding assay, as provided herein, a mixture is formed of two oligonucleotides which are effective, under appropriate conditions of temperature, ion concentration, etc., to hybridize by Watson-Crick base pairing. Typically, the oligonucleotides are complementary, and are generally of the same length. The first oligonucleotide is labeled with a first group effective to produce a detectable signal, and the second oligonucleotide includes a second group which is effective to detectably alter this signal when the first and second sequences convert from single-stranded to double stranded conformation, i.e., upon sequence complementary hybridization. Preferably, the first oligo is labeled at its 3' or 5' end, and the second oligonucleotide includes the second group at its 5' or 3' end, respectively.

An alternative arrangement (see Cantor, 1996) is that in which both first and second groups are on a single oligonucleotide which maintains the groups in proximity by assuming a "hairpin" conformation. When the oligonucleotide hybridizes with a second oligonucleotide, the groups become separated, and any proximity-dependent interaction between them is disrupted. Such a system could also be applied to certain embodiments of the assays described herein; however, in most instances, the presence of one interacting group on each oligo, as described above, is preferred.

A1. Detection Systems

A number of first and second group pairs may be used to provide a detection system. For example, the first group may be a fluorescent group (F) such as fluorescein. Any of the many other fluorescent dyes known in the art and suitable for oligonucleotide labeling may also be used; see, for example, Haugland, 1996. These include rhodamine, Texas Red, lucifer yellow, and EDANS (5-((2-aminoethyl)amino) naphthalene-1-sulfonic acid, sodium salt), and the like. The second group (Q) is effective to detectably alter a fluorescent signal emitted from the fluorescent group when the first and second sequences hybridize to form a duplex. In one embodiment, the second group quenches the fluorescent signal, e.g. when the second group is DabCyl™ (4-(4-dimethylaminophenylazo)benzoic acid), a known "universal" quencher. In this case, hybridization of the sequences results in a decrease in the observed level of fluorescence. Alternatively, the second group may be a second fluorescent group, effective to absorb the fluorescent radiation and re-emit it at a different wavelength, in a process known as FRET (fluorescence resonance energy transfer). The use of various fluorescence-based systems for detection of hybridization events, i.e. as probes in DNA assays, has been described, e.g. by Morrison et al., 1989, 1993; and Tyagi et al., 1996, 1998.

In another embodiment, the first group is a radioactive group, and the second group is a scintillant. Such a system is used in the technique known as scintillation proximity assay (SPA), described in U.S. Pat. Nos. 4,382,074 and 4,271,139, herein incorporated by reference. Use of this technique in biological assays is also described in U.S. Pat. Nos. 5,789,179 and 5,665,562, also incorporated by reference. In this assay format, the signal observed is dependent upon the proximity of a labeled molecule, bound to special scintillating beads, to weak β-emitting (i.e. radiolabeled) compounds. When a radioactive atom decays, it releases sub-atomic particles, such as electrons. The distance these particles will travel through an aqueous medium is limited and is dependent on the nature of the radioactive atoms. If a radioactive atom such as $^{33}P$ is in proximity to an SPA bead, which contains scintillant, electrons can reach the beads and stimulate the scintillant to emit light. However, if the radioactive atom is distant from the beads, the electrons do not reach the scintillant, and no light is emitted.

This technology can be applied to studies of ligand binding as disclosed herein. Example 13, below, describes the use of the assay in a high throughput screening method, using the SPA detection system. In this example, the first oligonucleotide is labeled with biotin, and is then tightly bound to streptavidin-coated SPA beads via the strong biotin/streptavidin interaction. These beads are impregnated with scintillant. The second oligonucleotide is labeled with a weak β-emitter, such as $^3H$ or $^{33}P$ The radioactive second oligonucleotide is mixed with a solution of the beads under conditions at which the first and second oligonucleotides exist primarily as single strands, as described above. The signal will thus be low, as the oligonucleotides are non-hybridized. When ligand is added, the duplex form is stabilized, and the increased proximity of the radioactive isotope (e.g., $^3H$, $^{33}P$) in the second oligonucleotide causes the bead to which the first oligonucleotide is bound to scintillate. A signal thus indicates the presence of an effective binding ligand molecule; test sequences giving higher signals indicate the relative preference for different sequences.

In another embodiment, one of the first and second groups is chemiluminescent groups, and the two groups participate in a chemiluminescent reaction; light is thereby emitted when the reaction takes place. Many such reactions are known in the art. (See, for example, Campbell, 1988; Nieman, 1995.) Useful liquid-phase chemiluminescent reactions, often used in detection systems, include the oxidation of luciferin, catalyzed by luciferase, and the oxidation of lucigenin to N-methylacridone in the presence of base and an Fe(II) catalyst. Luminol (5-amino-2,3-dihydro-1,4-phthalazinedione) also reacts with oxidants such as $H_2O_2$ in the presence of base and a copper(II) or iron(III) catalyst to produce an excited state product (3-aminophthalate, 3-APA) which gives off light at approximately 425 nm.

In principle, any method which can detect the transition from single-stranded to double stranded DNA could be used to study ligand binding using indicator oligos such as those shown in Table I. This could include methods which detect differences in properties, such as spectral characteristics or chromatographic mobility, between the single stranded and double stranded oligonucleotides. In such cases the oligonucleotides need not be labeled. For example, single-stranded oligos usually migrate differently from duplex nucleic acids during electrophoresis on polyacrylamide gels. This difference in migration could be used to observe the single-strand to duplex transition caused by the binding of ligands to nucleic acids. In such an assay, a mixture of the two oligonucleotides would be mixed, together with increasing concentrations of a test compound. One of the strands could be labeled with $^{32}P$ in order to allow visualization after electrophoresis. Drug binding would be observed directly as a change in mobility of the oligo upon drug binding due to the stabilization of the duplex nucleic acid.

Liquid chromatographic and mass chromatographic methods which can distinguish single-stranded oligos from double-stranded oligos are also available. For example, the ligand dependent retention of the second strand of the indicator on a magnetic bead could be detected using mass spectrometry methods. These methods could also be applied to this ligand-binding assay.

The CD (circular dichroism) spectrum of nucleic acids is extremely sensitive to structural conformation, and single-stranded oligos have very different CD spectra from double-stranded oligos. This large spectral difference could be the basis of a detection scheme for studying ligand binding to nucleic acids. Fluorescence anisotropy could also be used to observe the ligand-induced hybridization of duplex nucleic acids. Biosensor based instruments can detect very small changes associated with almost any binding event. This technology uses an evanescent field to measure minute changes in refractive index and thickness at the resonant mirror sensor surface. DNA/DNA hybridization can be detected using this method. As in SPA, one of the strands could be immobilized with biotin onto a surface, and the biosensor would then detect the drug-dependent binding of the second strand in the indicator duplex. The two strands could also be labeled with functional groups to cause a larger increase in signal upon hybridization.

A2. Assay Procedure

The addition of a binding ligand to an oligonucleotide indicator pair, as defined herein, will generally favor the formation of the duplex, bringing the interacting groups into proximity. This is illustrated for a fluorescence quenching system in FIG. 1A, where hybridization causes the fluorescent signal to decrease. Affinity of binding of a range of ligands to a known sequence, or of a variety of sequences to a single ligand, can thus be evaluated based on the magnitude of this effect, as illustrated in FIG. 1B.

For maximum effectiveness of the assay, in terms of range of signal, the system is designed such that, in the absence of the ligand, the oligonucleotides exist primarily in single-stranded form. Variables that may be adjusted include the size and sequence of the oligos themselves and experimental conditions such as temperature, salt level, etc. In one embodiment, the assay is performed at a temperature that is somewhat higher than the $T_m$ of the duplex under the conditions (e.g. salt concentration) of the assay. The assay may be performed at or near room temperature but is not limited to any particular temperature. In a preferred embodiment, the assay is performed isothermally, that is, at a substantially constant temperature.

The specific examples described below employ fluorescence quenching as the detection system, although other detection systems, such as described above, could also be used. In these examples, because conditions are adjusted to maintain the oligonucleotides in single-stranded form in the absence of the ligand, the assay starts with the system at a high or maximum level of fluorescence, and fluorescence generally decreases, depending on binding affinity, as the ligand is added.

Figure 2B:
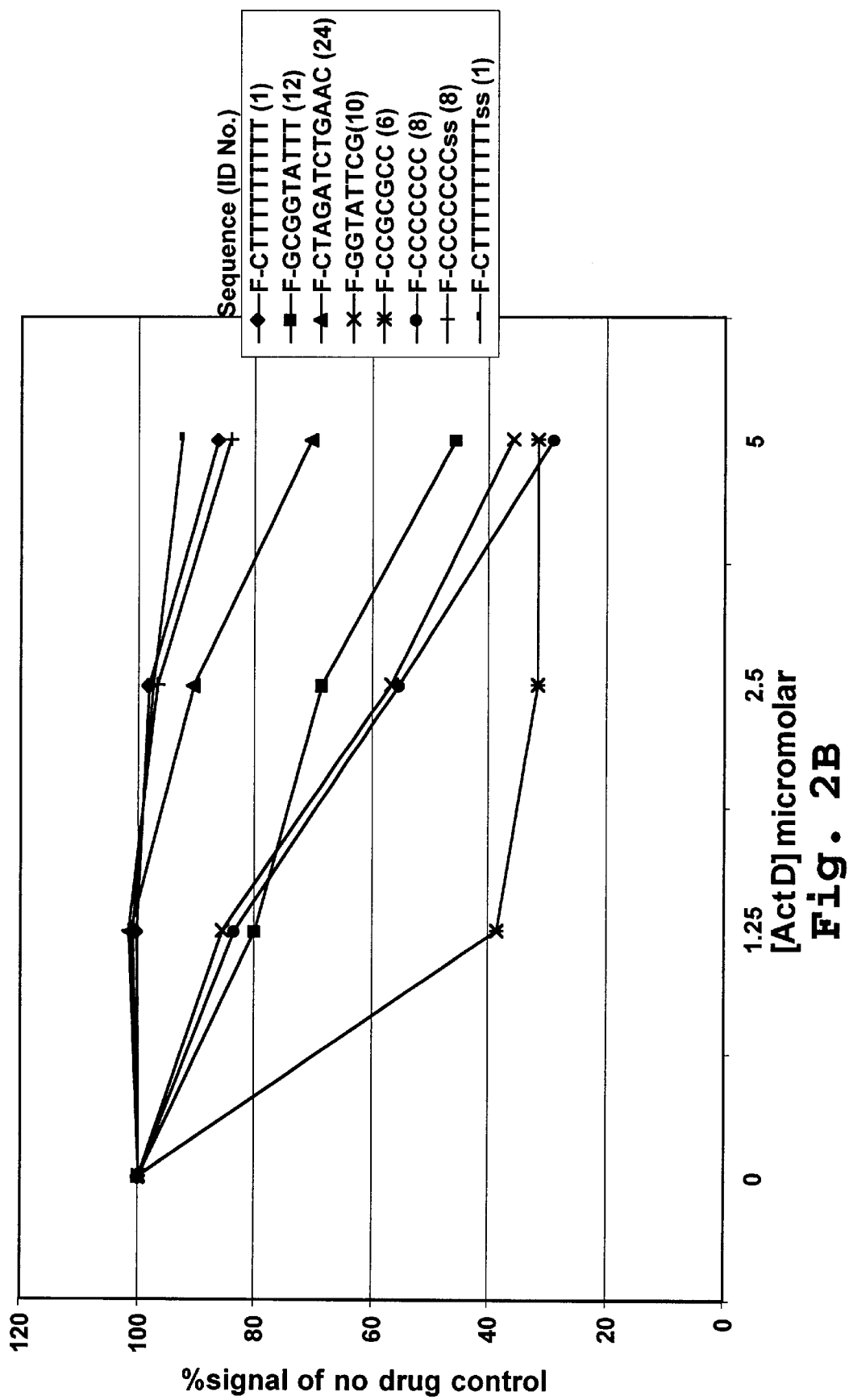
Figure 2C:
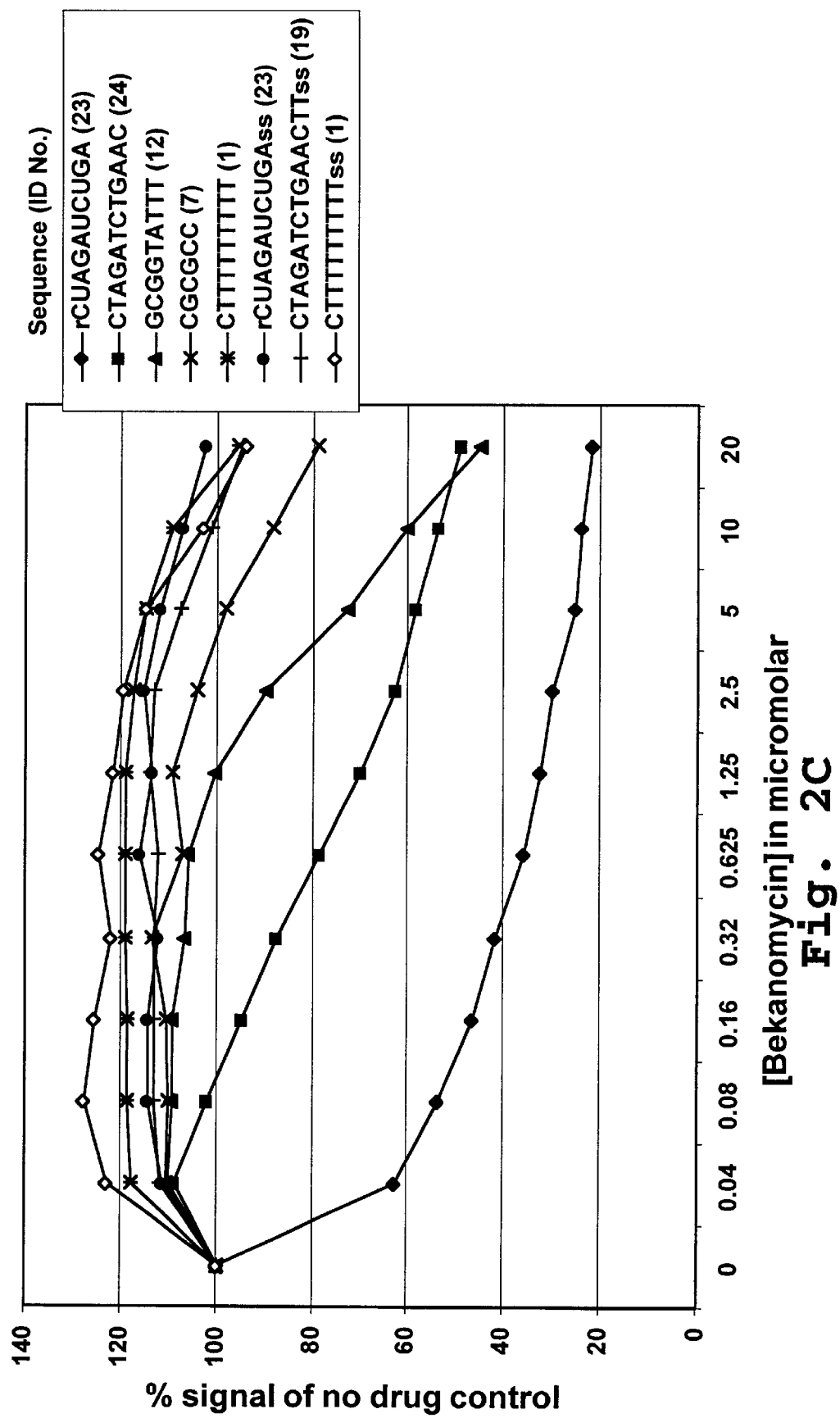

Binding curves representing the interaction of the drugs netropsin, bekanomycin, and actinomycin D with various oligos, in applications of the direct assay, are shown in FIGS. 2A–2C. The legends show the sequence of one strand of each F-Q indicator pair. These "indicator" oligonucleotides are also shown in Table I. The different types of oligos, as shown, allow side by side comparison of ligand binding with DNA sequences, RNA sequences, and A/T rich, G/C rich, or mixed sequences of both types. In Table I, most of the complementary strands are not shown. The complementary strands that are shown are indicated by (−) and are written in a 3'-5' orientation to show possible base pairing with the (+) strand.

TABLE I

Indicator Oligonucleotides

| Seq. ID No. | Type | Sequence |
|---|---|---|
| 1 | A/T rich DNA | 5'-CTTTTTTTTT-3' |
| 2 | A/T rich DNA | 5'-CTTTATTATTTT-3' |
| 3 | Mixed DNA | 5'-CTCTCTCTC-3' |
| 4 | Inosine containing (+) | 5'-CCIICCIICC-3' |
| 5 | Inosine containing (−) | 5'-GGCCIICCGG-5' |
| 6 | G/C rich DNA | 5'-CCGCGCC-3' |
| 7 | G/C rich DNA | 5'-CGCGCG-3' |
| 8 | G/C rich DNA | 5'-CCCCCCC-3' |
| 9 | poly A/T DNA | 5'-GATATATATAG-3' |
| 10 | Mixed DNA | 5'-GGTATTCG-3' |
| 11 | Mixed DNA | 5'-GCGTATTT-3' |
| 12 | Mixed DNA | 5'-GCGGTATTT-3' |
| 13 | G/C rich DNA | 5'-CGCGCC-3' |
| 14 | Mixed RNA (+) | 5'-CUAGAUCUGAACUU-3' |
| 15 | Mixed RNA (−) | 3'-GAUCUAGACUUGAA-5' |
| 16 | Mixed RNA (−) | 3'-GAUCUAGACUUG-5' |
| 17 | Mixed RNA (−) | 3'-GAUCUAGACU-5' |
| 18 | Mixed RNA (−) | 3'-GAUCUAGAC-5' |
| 19 | Mixed DNA (+) | 5'-CTAGATCTGAACTT-3' |
| 20 | Mixed DNA (−) | 3'-GATCTAGACTTGAA-5' |
| 21 | Mixed DNA (−) | 3'-GATCTAGACTTG-5' |
| 22 | Mixed DNA (−) | 3'-GATCTAGACT-5' |
| 23 | Mixed RNA | 5'-CUAGAUCUGA-3' |
| 24 | Mixed DNA | 5'-CTAGATCTGAAC-3' |

In the Figure legends, RNA oligos are denoted by an "r" at the beginning of the sequence, and single stranded controls by "ss" at the end of the sequence. These single stranded sequences are used alone in control experiments, which thus employ only an "F" strand and no complementary quenching strand. Any quenching of fluorescence that is not due to hybridization can thus be accounted for. Maximum quenching expected on complete hybridization of these oligos is 85–90%; therefore some signal; remains after complete hybridization. The signal is plotted so that it is normalized to the control signal in the absence of ligand.

Netropsin has been shown in previous studies to bind preferentially to A/T rich regions of DNA. FIG. 2A shows the effect of adding increasing amounts of netropsin to mixtures of selected F/Q indicator oligonucleotide pairs, whose sequences are given in Table I. The sequence of the "F" strand of each pair is given in the figure legend, along with three single stranded controls, as indicated. From the data shown in FIG. 2A, it can be seen that netropsin strongly prefers the sequence 5'-CTTTTTTTTT-3' (SEQ ID NO: 1). Netropsin also binds well to the sequence 5'-GCGGTATTT-3' (SEQ ID NO: 12), which is a useful "indicator" probe (as discussed below), having both C/G and A/T rich sequences. The drug does not bind well to the G/C rich sequence 5'-CGCGCC-3' (SEQ ID NO: 7) or to RNA (5'-rCUAGAUCUGA-3'; SEQ ID NO: 23); for these oligos, the change in fluorescence was similar to that seen for the single-stranded controls.

FIGS. 2B and 2C show similar experiments performed with actinomycin D, which is generally believed to prefer binding to C/G rich regions of DNA, and bekanomycin, an RNA binding drug. Again, the "F" strand of each indicator pair is shown in the legend, along with single stranded controls. As shown in FIG. 2B, actinomycin D shows binding only to the C/G containing sequences (SEQ ID NOS: 6, 8, and 12) at concentrations up to 5 $\mu$M. Bekanomycin shows a very strong preference for the double stranded RNA probe (SEQ ID NO: 23) over all of the other test oligos (FIG. 2C).

Figure 2D:
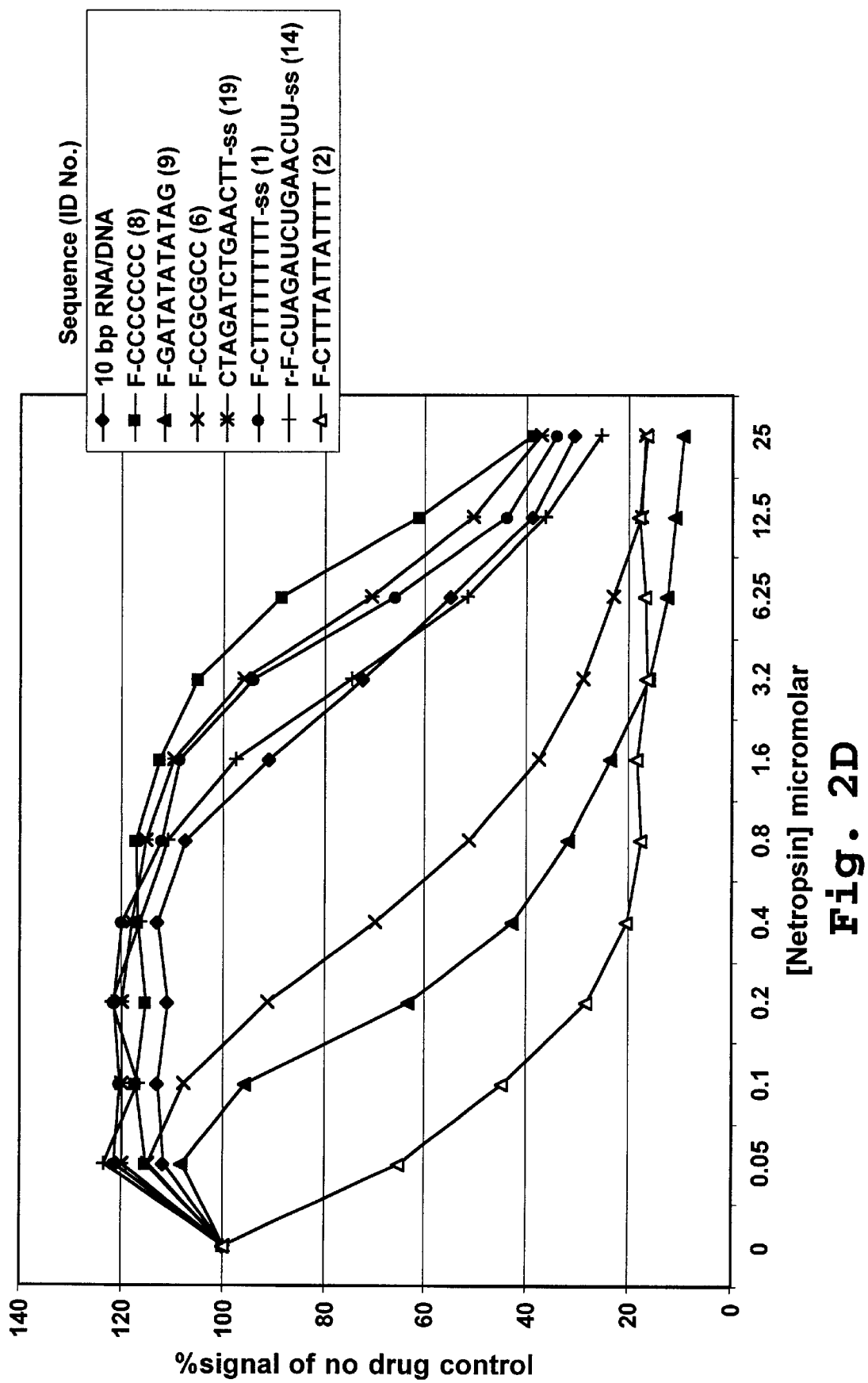
FIG. 2D shows the results of an experiment similar to that of FIG. 2A, carried out without the addition of a nonspecific binding agent (transfer RNA)

Interference from non-specific binding, based on electrostatic attraction, for example, may be reduced by addition of a competing species. For example, tRNA was added to the DNA binding experiment shown in FIGS. 2A and 2B. FIG. 2D shows the results of the study similar to that carried out for FIG. 2A, but without added tRNA. It can be seen that the presence of tRNA increased the distinction between the strongly binding sequence(s) and the remaining sequences. For RNA binding studies, non-specific binding compounds such as heparin or poly-dIdC may be used in place of tRNA.

One advantage of this assay, as opposed to conventional assays based on melting, is that it can be carried out at a substantially constant temperature, with the ligand added in increasing concentration. Preferably, the assays are performed at a temperature somewhat higher than the $T_m$ of the duplex under the assay conditions, so the oligonucleotides will be in single-stranded form at the outset of the assay; this gives the greatest range of signal, as the oligonucleotides convert from fully (or primarily) single-stranded to double-stranded. If desired, the length and composition of the oligonucleotides, and experimental conditions such as salt concentration, may be adjusted so that the assay can be carried out at or near room temperature. This is particularly applicable for shorter oligonucleotides. However, the assay is not limited to any particular temperature.

Because the assay is based on a shift in equilibrium, it may be used for transiently binding ligands. It is also suitable for very small ligands, such as metal ions. In contrast to labor-intensive methods such as DNA footprinting, the assay allows very rapid determination and comparison of ligand binding to RNA vs. DNA, and of G/C rich vs. A/T rich sequences. In this sense, it is well suited for high throughput screening methods, which can be performed in an automated mode using commercially available systems. In addition, the assay gives information pertaining to only the actual binding site of the ligand, even for large ligands, such as proteins. Previous methods such as DNA footprinting, as noted above, indicate only the region of the oligonucleotide masked by the protein, which may be much larger than the binding site.

For larger ligands, longer oligonucleotide sequences than those shown in Table I may be required for binding. In such cases, a fairly high temperature may be required to maintain these sequences in single-stranded form even in the absence of the ligand. In such cases, a kinetic displacement assay, performed at lower temperatures, preferably at ambient temperatures, may be preferred. Such assays are described further below.

Although the assay is preferably carried out in an isothermal mode, it may also be run in a more conventional melting-type format, where change in extent of hybridization is observed as a function of temperature. For example, in an assay designed to screen a large number of drugs for preference for RNA or DNA binding, arrays of wells are provided, each containing an RNA indicator pair labeled with a first dye, and a similar-sequence DNA indicator pair labeled with a second dye. The use of different fluorescent dyes permits simultaneous detection of different species. A test ligand is added to each well, and the wells are gradually heated. Ligands which bind either RNA or DNA (or both) will increase the $T_m$ of the respective indicator pairs, thus affecting the change in fluorescence with temperature. DNA vs. RNA binding is distinguished by the use of the two dyes, allowing detection at separate wavelengths. A similar format could be used to simultaneously screen a single drug for binding to a plurality of nucleic acid sequences.

B. Competitive Assay

Direct assays, as described above, are useful for first level screening of oligonucleotide-ligand binding, e.g. preference for DNA vs. RNA, or A/T vs. C/G rich sequences. In a "next-stage" assay, termed herein a competition or competitive assay, a strong binding oligonucleotide for a particular ligand, such as determined from direct assays, is used as an "indicator" for competitive studies, which give a further level of detail about drug binding preferences.

A competition experiment starts with first and second indicator oligos, as described above, containing, respectively, a first group effective to produce a detectable signal, and a second group effective to alter this signal. At the beginning of the assay, the ligand is bound to a duplex of the sequences. Again, experimental conditions of temperature, salt content, etc. are preferably adjusted such that, in the absence of the ligand, the oligonucleotides would exist primarily in single-stranded form. As noted above, the preferred temperature is somewhat higher than the $T_m$ of the duplex (in the absence of ligand) under the conditions of the assay. If desired, for the sake of convenience, conditions may be adjusted so that the assay can be carried out at or near room temperature.

As above, the first and second groups are preferably located at the 5' and 3' ends, respectively, of the first and second oligos. Various detection systems for the assays, based, for example, on fluorescence quenching or reemission, SPA, or chemiluminescence, are described above. Competitive assays using fluorescence quenching are described in further detail below.

At the beginning of the assay, the indicator sequences form a duplex in the presence of the ligand, so fluorescence is at a minimum for the system. (When other detection systems are used, the signal observed will be that in which the first and second interacting groups, such as a radioactive emitter and scintillant, are in close proximity.) A "competitor" sequence, having no quenching group, is then added, typically as a duplex with its complementary sequence. The competing sequence tends to remove the ligand from the indicator duplex at concentrations that become lower as the affinity of the competing sequence for the ligand becomes greater. Alternatively, the competing sequence removes the ligand more effectively at concentrations equimolar with the indicator duplex as the affinity of the competing sequence for the ligand becomes greater. As the ligand is removed, the indicator sequences denature to single-stranded form, quenching is no longer effective (in an F/Q system), and fluorescence increases.

The groups of "competitor" oligos shown in Tables II–V provide a useful selection of sequence motifs for screening of a ligand which is believed to prefer A/T rich DNA sequences. Similar collections could be provided for C/G sequence motifs. As shown in the following examples, preferences among single-base variations in sequences 4–5 nucleotides in length, and the precise length of critical binding sequences, can be determined by this method.

Competitor oligonucleotides can include duplex DNA, duplex RNA, duplex RNA/DNA, and single stranded polynucleotides. Single stranded polynucleotides can fold into secondary structures which can effectively compete for ligand binding. These secondary structures include hairpins, bulges, pseudoknots, adducted polynucleotides, four way junction polynucleotides, etc.

Figure 3:
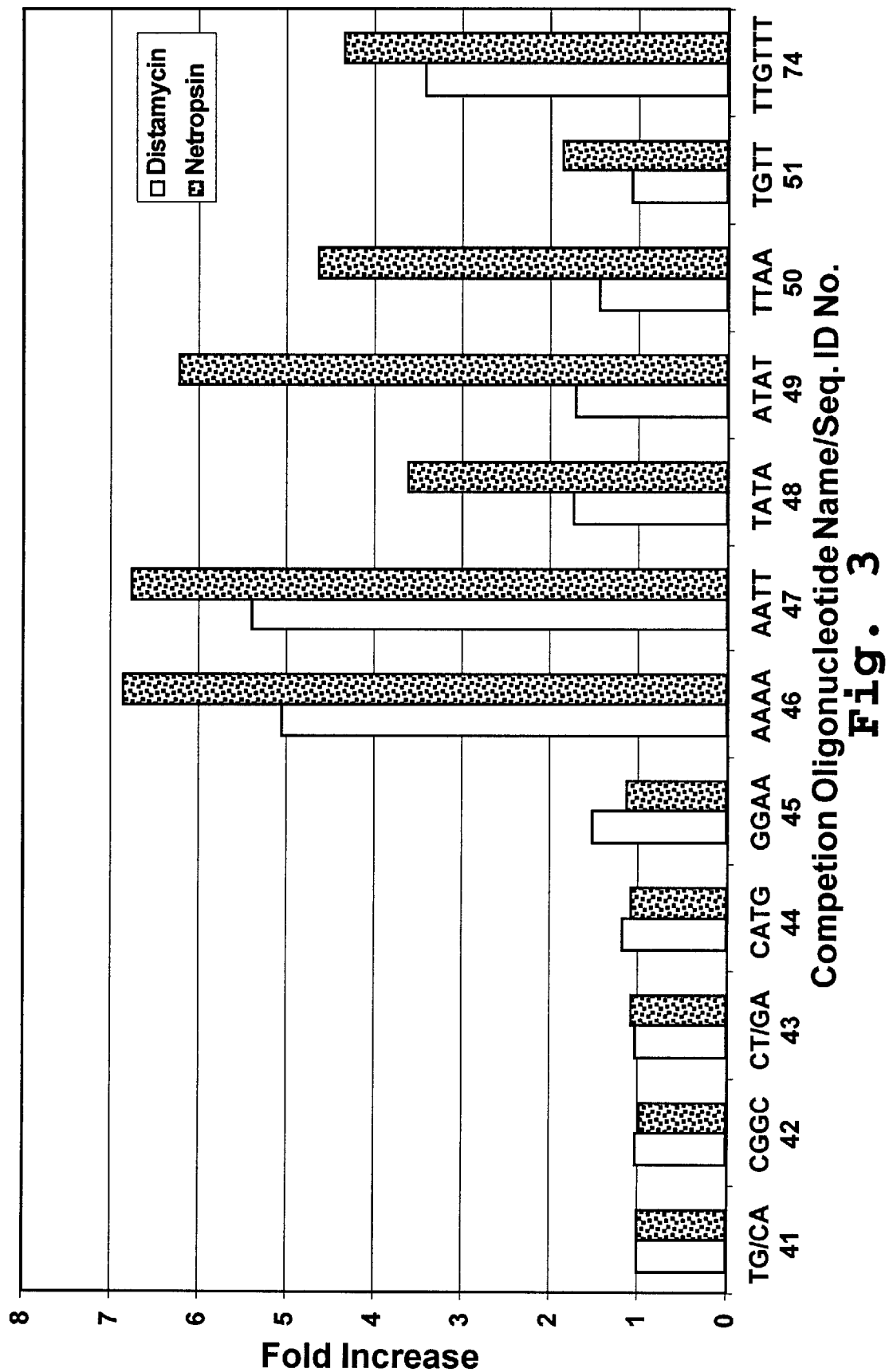
FIG. 3 shows the increase in fluorescence upon adding competitor oligos containing various sequence motifs to an F/Q "indicator" duplex having bound distamycin or netropsin, respectively, in a competitive assay.

Results of a typical competition assay are shown in FIG. 3, where the fluorescent signal of netropsin and distamycin bound to a duplex of an A/T rich "indicator" molecule (5'-CTTTATTATTTT-3'; SEQ ID NO: 2, and its complement) is compared to the signal in the presence of equal concentrations of different competitor oligos, whose sequences (SEQ ID NOs: 41–51 and 74) are listed in Table II. An increase in signal, as described above, indicates that the drug is binding the unlabeled competitor oligo rather than the indicator molecule, causing a shift in equilibrium back towards single-stranded indicator oligos.

TABLE II

Sequences of Competition Oligos

| Seq. ID No. | Name | Sequence |
|---|---|---|
| Mixed Sequence Controls: | | |
| 41 complement | TG/CA | 5'-GTGTGTGTGTGTG-3' 3'-CACACACACACAC-5' |
| 42 | CGGC | 5'-CCCGGCCGGCCC-3' 3'-GGGCCGGCCGGG-5' |
| 43 | CT/AG | 5'-CTCTCTCTCTCTC-3' 3'-GAGAGAGAGAGAG-5' |
| 44 | CATG | 5'-CATGTCAGTCGA-3' 3'-GTACAGTCAGCT-5' |
| 45 | GGAA | 5'-GGAAGGAAGGAA-3' 3'-CCTTCCTTCCTT-5' |
| Four bp A + T sites: | | |
| 46 | AAAA | 5'-CCCGAAAACGCC-3' 3'-GGGCTTTTGCGG-5' |
| 47 | AATT | 5'-CCCGAATTCGCC-3' 3'-GGGCTTAAGCGG-5' |
| 48 | TATA | 5'-CCCGTATACGCC-3' 3'-GGGCATATGCGG-5' |
| 49 | ATAT | 5'-CCCGATATCGCC-3' 3'-GGGCTATAGCGG-5' |
| 50 | TTAA | 5'-CCCGTTAACGCC-3' 3'-GGGCAATTGCGG-5' |
| 51 | TGTT | 5'-CCCGTGTTCGCC-3' 3'-GGGCACAAGCGG-5' |
| 74 | TTGTTT | 5'-CCGTTGTTTCCG-3' 3'-GGCAACAAAGGC-5' |

The data in FIG. 3 show that A/T rich competitor sequences were more effective in removing ligand from the indicator duplex, causing an increase in fluorescence as the indicator duplex denatures. It is thus clear that netropsin and distamycin are relatively specific ligands that strongly prefer A/T rich DNA, consistent with the results shown in FIG. 2.

Figure 4:
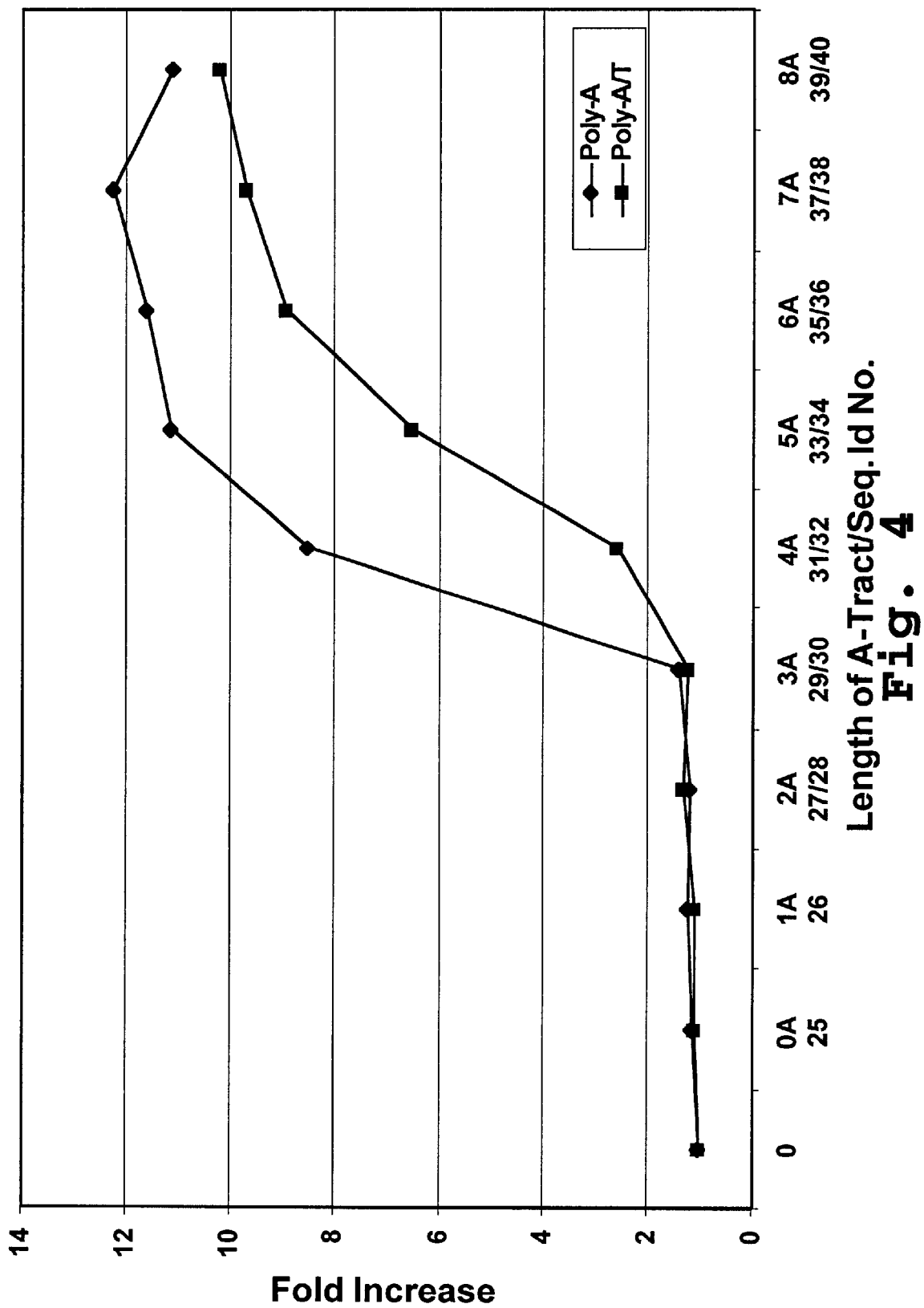
FIGS. 4 and 5 show the increase in fluorescence upon adding competitor oligos having different lengths of poly-A and poly-TA tracts to an F/Q indicator duplex having bound distamycin or netropsin, respectively.
Figure 5:
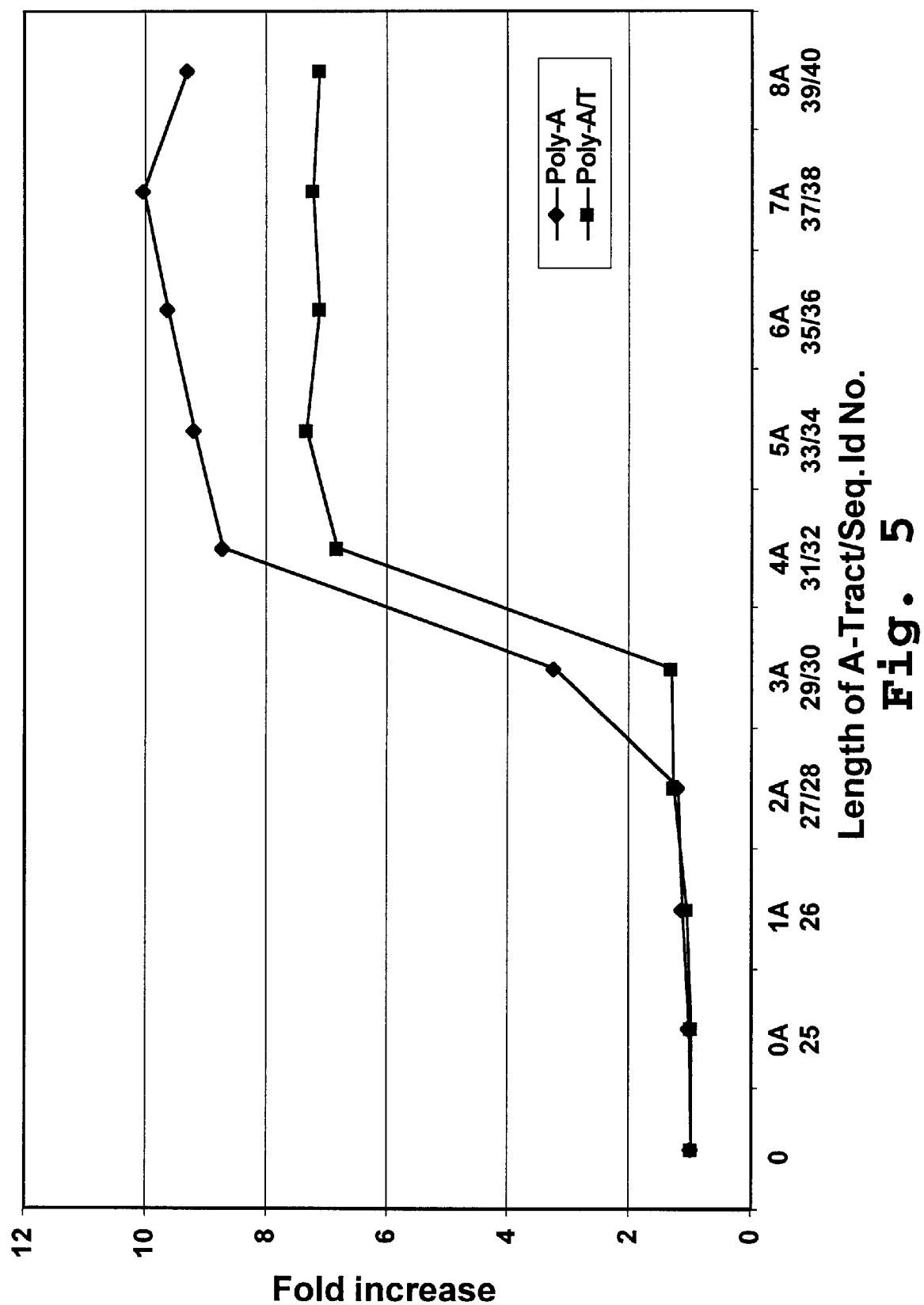

To further explicate the specificity of these drugs, i.e., to determine the preferred length of A/T rich binding determinants for each drug, a competition study was done using A-tracts of increasing length. Competitor oligos containing two different types of A-tracts, either homopolymer poly-A type or alternating poly-TA type, were used. These oligos are listed in Table III (SEQ ID NOs: 25–40). The results of the study are shown in FIGS. 4 and 5. The data shows that both drugs bind relatively weakly to A-tracts of 3 or less, but binding sharply increases for 4 bp A-tracts, particularly in the case of poly-A. The results also show that for both drugs a slightly longer poly-TA tract is needed to compete for drug binding than the corresponding poly-A tract. This is consistent with the data shown in FIG. 3, indicating that these drugs, especially distamycin, strongly prefer binding to AAAA over TATA. In fact, for both drugs, the most favored sequences of those examined are those containing AAAA/TTTT and AATT (FIG. 3).

TABLE III

Sequences of Competition Oligos

| Seq. ID No. | Name | Poly-A | | Poly-A/T |
|---|---|---|---|---|
| 25 complement | 0 A | 5'-CCCGGCCGGCCC-3' 3'-GGGCCGGCCGGG-5' | | Same Oligo |
| 26 complement | 1 A | 5'-CCCGGACGGCCC-3' 3'-GGGCCTGCCGGG-5' | | Same Oligo |
| 27, 28 complements | 2 A | 5'-CCCGGAACCGCC-3' 3'-GGGCCTTGGCGG-5' | | 5'-CCCGGTACCGCC-3' 3'-GGGCCATGGCGG-5' |
| 29, 30 | 3 A | 5'-CCCGAAACCGCC-3' 3'-GGGCTTTGGCGG-5' | | 5'-CCCGATACCGCC-3' 3'-GGGCTATGGCGG-5' |
| 31, 32 | 4 A | 5'-CCCGAAAACGCC-3' 3'-GGGCTTTTGCGG-5' | | 5'-CCCGATATCGCC-3' 3'-GGGCTATAGCGG-5' |
| 33, 34 | 5 A | 5'-CCCAAAAACGCC-3' 3'-GGGTTTTTGCGG-5' | | 5'-CCCTATATCGCC-3' 3'-GGGATATAGCGG-5' |
| 35, 36 | 6 A | 5'-CCCAAAAAAGCC-3' 3'-GGGTTTTTTCGG-5' | | 5'-CCCTATATAGCC-3' 3'-GGGATATATCGG-5' |
| 37, 38 | 7 A | 5'-CCAAAAAAAGCC-3' 3'-GGTTTTTTTCGG-5' | | 5'-CCATATATAGCC-3' 3'-GGTATATATCGG-5' |
| 39, 40 | 8 A | 5'-CCAAAAAAAACC-3' 3'-GGTTTTTTTTGG-5' | | 5'-CCATATATATCC-3' 3'-GGTATATATAGG-5' |

The succeeding examples show the influence of the sequence determinants outside of these four base pair core elements on distamycin and netropsin binding. It was expected that, because distamycin had been shown to interact with more than 4 base pairs, sequences flanking the high affinity AATT site may be important. This was investigated using a set of competitor oligos containing all possible sequences in the arrangement 5'-XAATTY-3' (SEQ ID NOs 64–73; see Table IV). Because AATT is a palindrome, there are ten unique combinations of this sequence.

TABLE IV

Sequences of Competition Oligos: 5'-XAATTY-3' Series
5'-CCCXAATTYGCC-3' SEQ ID NO:80
3'-GGGYTTAAXCGG-5' complement

| Seq. ID No. | Name (XY/XY) | Sequence |
|---|---|---|
| 64 complement | CC/GG | 5'-CCCCAATTCGCC-3' 3'-GGGGTTAAGCGG-5' |
| 65 | CA/TG | 5'-CCCCAATTAGCC-3' 3'-GGGGTTAATCGG-5' |
| 66 | AG/CT | 5'-CCCAAATTGGCC-3' 3'-GGGTTTAACCGG-5' |
| 67 | CG | 5'-CCCCAATTGGCC-3' 3'-GGGGTTAACCGG-5' |
| 68 | AC/GT | 5'-CCCAAATTCGCC-3' 3'-GGGTTTAAGCGG-5' |
| 69 | AA/TT | 5'-CCCAAATTAGCC-3' 3'-GGGTTTAATCGG-5' |
| 70 | AT | 5'-CCCAAATTTGCC-3' 3'-GGGTTTAAACGG-5' |
| 71 | GA/TC | 5'-CCCGAATTAGCC-3' 3'-GGGCTTAATCGG-5' |
| 72 | TA | 5'-CCCTAATTAGCC-3' 3'-GGGATTAATCGG-5' |
| 73 | GC | 5'-CCCGAATTCGCC-3' 3'-GGGCTTAAGCGG-5' |

Figure 6:
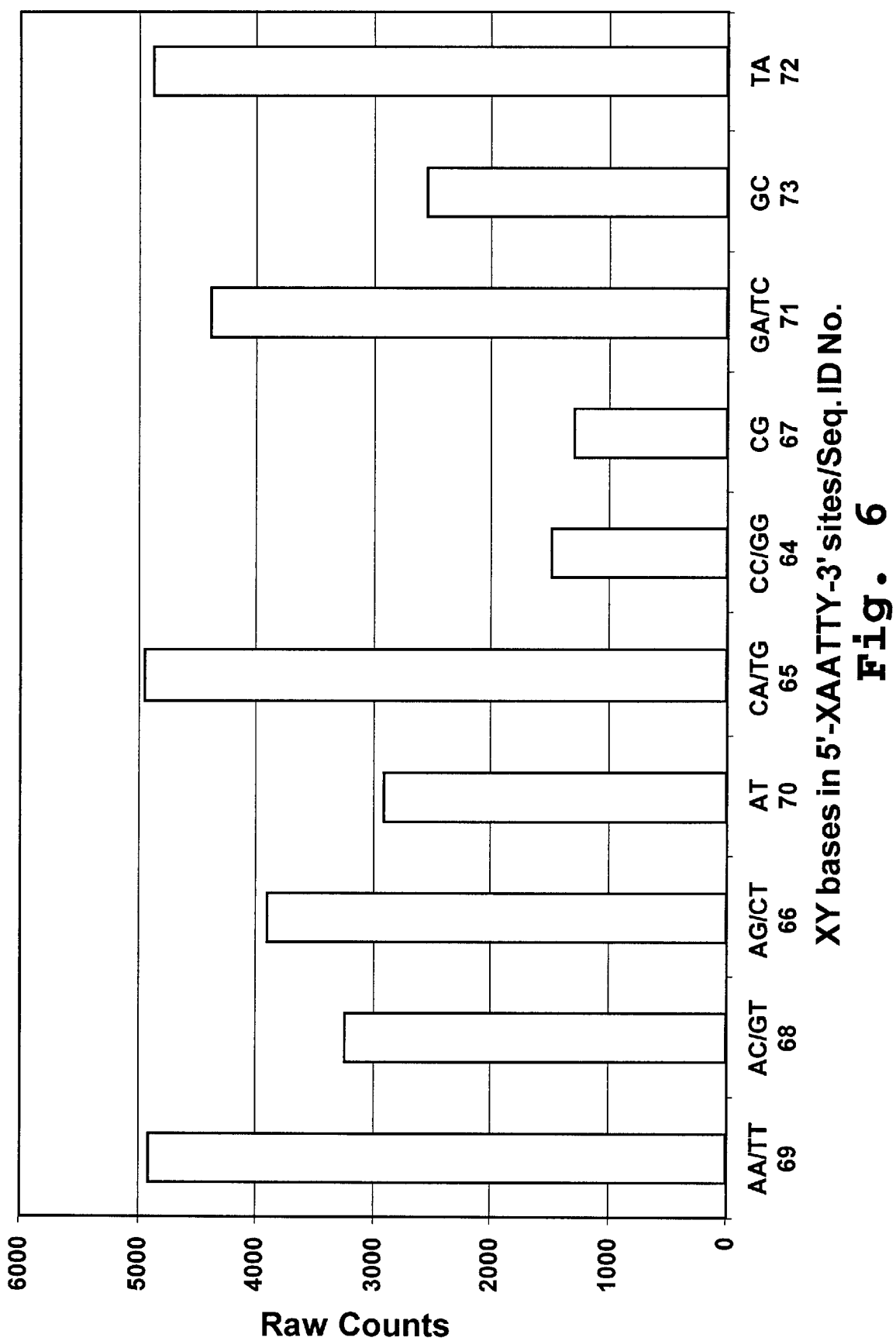
FIGS. 6 and 7 show the increase in fluorescence upon adding a series of competitor oligos, having different bases flanking an AATT sequence, to an F/Q indicator duplex having bound distamycin or netropsin, respectively.
Figure 7:
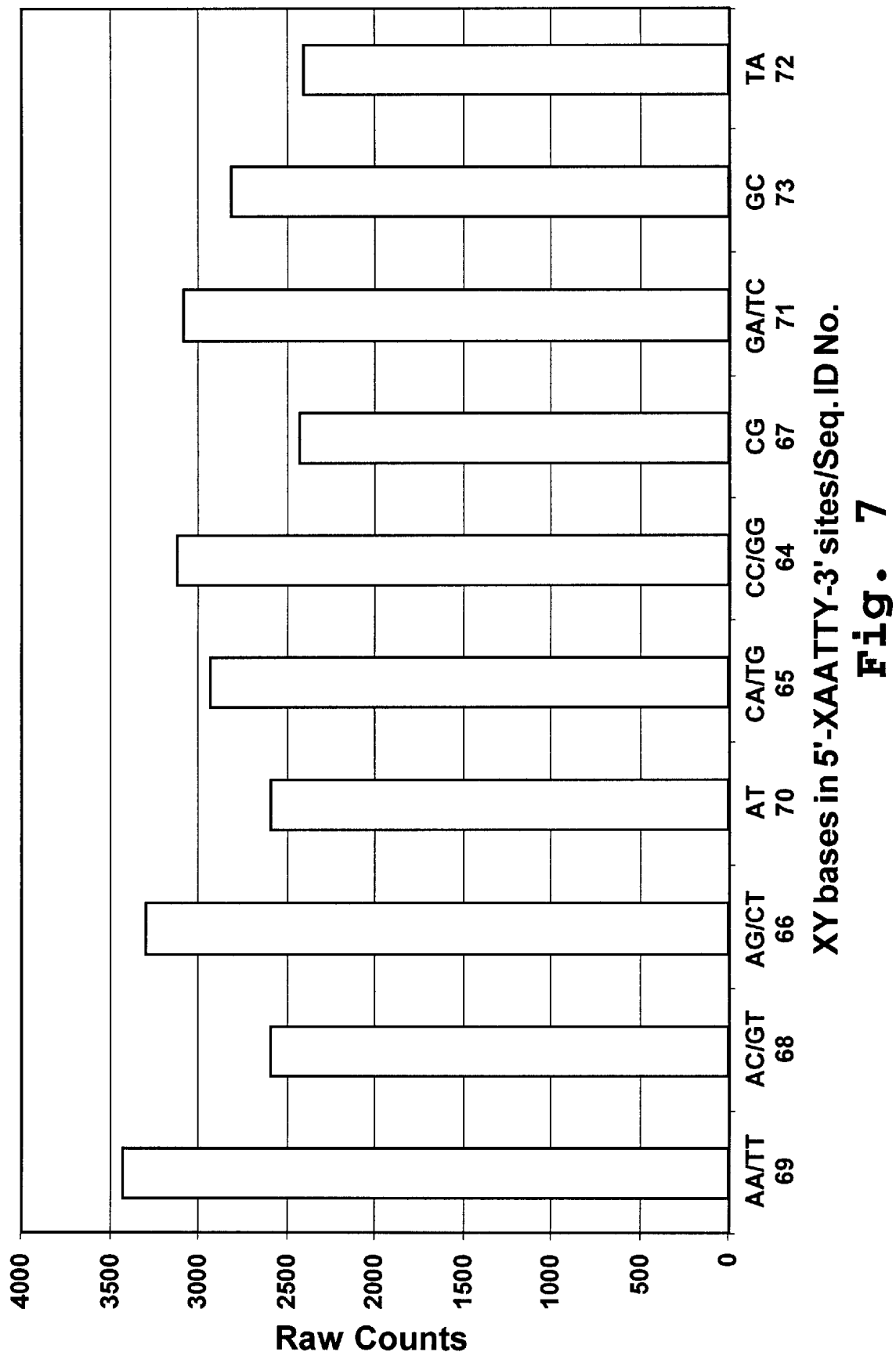

The results, shown in FIGS. 6 and 7, indicate that distamycin is much more sensitive, as expected, to the bases at the edge of the AATT site than is netropsin. The X and Y combinations that competed most effectively for distamycin binding were AA/TT, CA/TG, GA/TC, and TA/TA (i.e., SEQ ID NOs: 69, 65, 71, and 72) (see FIG. 6). The common element in these combinations is an adenine (A) at the Y position, which generates the five base pair sequence 5'-AATTA-3'. One would therefore conclude that this is the preferred 5 bp binding site for distamycin.

Figure 8:
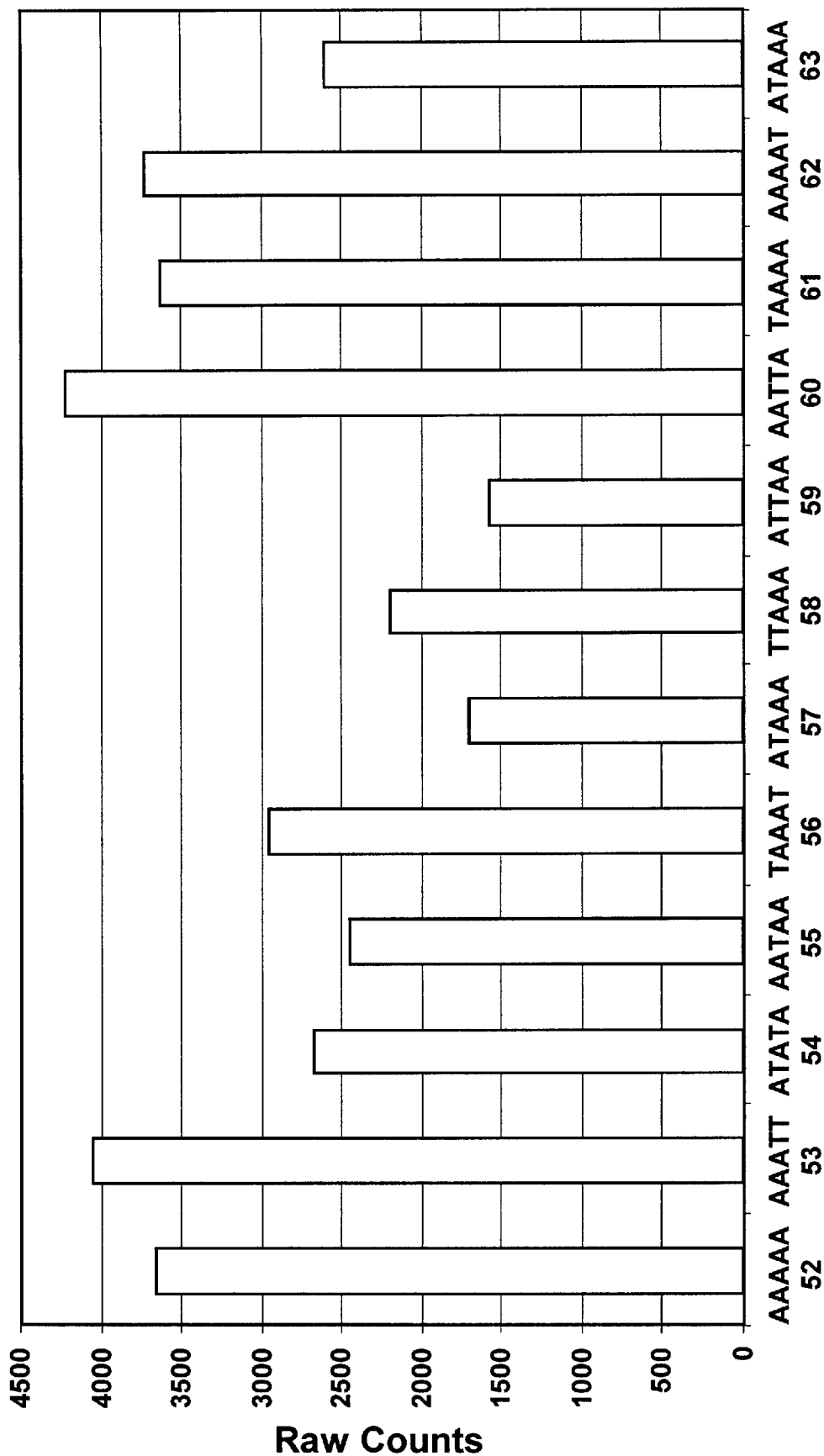
FIGS. 8 and 9 show the increase in fluorescence upon adding competitor oligos containing various 5-nucleotide A/T motifs to an F/Q indicator duplex having bound distamycin or netropsin, respectively.
Figure 9:
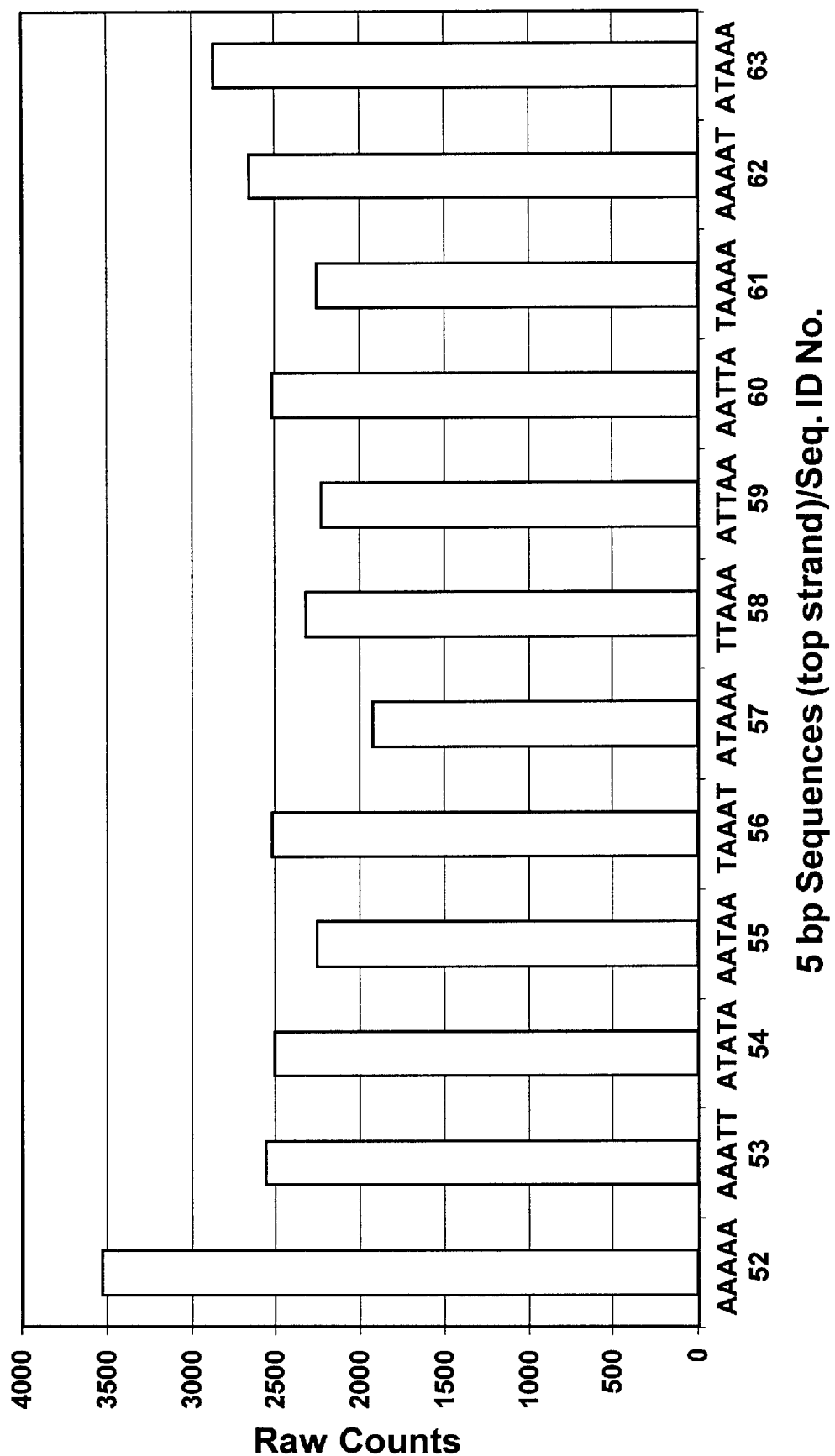

To further support this conclusion, an experiment was done using competitor oligos containing all possible 5 bp (A+T) binding sites (SEQ ID NOs: 52–63; Table V). The results, shown in FIG. 8, show that distamycin has relatively strong preferences for the various 5 bp A/T binding sites, and appears to bind most strongly to the site 5'-AATTA-3' (included in SEQ ID NO: 60), confirming the results of the previous example. Netropsin, on the other hand, shows considerably less discrimination for the various 5 bp sites, showing a slight preference for the AAAAA site (included in SEQ ID NO: 52) (FIG. 9).

TABLE V

Sequences of Competition Oligos: 5 bp A + T Sites

| Seq. ID No. | Name | Sequence |
| --- | --- | --- |
| 52 | AAAAA | 5'-CCCGAAAAACCG-3' |
| complement | | 3'-GGGCTTTTTGGC-5' |
| 53 | AAATT | 5'-CCCGAAATTCCG-3' |
| | | 3'-GGGCTTTAAGGC-5' |
| 54 | ATATA | 5'-CCCGATATACCG-3' |
| | | 3'-GGGCTATATGGC-5' |
| 55 | AATAA | 5'-CCCGAATAACCG-3' |
| | | 3'-GGGCTTATTGGC-5' |
| 56 | TAAAT | 5'-CCCGTAAATCCG-3' |
| | | 3'-GGGCATTTAGGC-5' |
| 57 | ATAAA | 5'-CCCGATAAACCG-3' |
| | | 3'-GGGCTATTTGGC-5' |
| 58 | TTAAA | 5'-CCCGTTAAACCG-3' |
| | | 3'-GGGCAATTTGGC-5' |
| 59 | ATTAA | 5'-CCCGATTAACCG-3' |
| | | 3'-GGGCTAATTGGC-5' |
| 60 | AATTA | 5'-CCCGAATTACCG-3' |
| | | 3'-GGGCTTAATGGC-5' |
| 61 | TAAAA | 5'-CCCGTAAAACCG-3' |
| | | 3'-GGGCATTTTGGC-5' |
| 62 | AAAAT | 5'-CCCGAAAATCCG-3' |
| | | 3'-GGGCTTTTAGGC-5' |
| 63 | ATAAA | 5'-CCCGATAAACCG-3' |
| | | 3'-GGGCTATTTGGC-5' |

The sensitivity of the assay is apparent from these examples. The assay also has the advantages of speed and simplicity, as in the direct assay, when compared to previous methods used to obtain comparable information. Further, it is not necessary for the competitive oligonucleotide to be labeled or to attain any particular "quenching" conformation. This feature allows species such as single stranded or folded RNA, which can have highly complex secondary structure, to be tested as easily as linear duplex DNA. Further, as noted for the direct assay, a variety of binding ligands, from single ions to large protein complexes, may be used.

C. Kinetic Strand Displacement Assay

This version of the assay is based on the displacement of a shorter strand within an indicator duplex by a longer strand. Because this displacement generates a longer, more stable, duplex, it is favored by free energy considerations. Again, a duplex of first and second sequences, as described above, is used, but in this assay, the strands differ in length, thus creating a single stranded overhang region. In a fluorescence quenching assay format, for example, the "F" strand is longer than the "Q" strand. In most cases, a minimum overhang region of about 4–20 nucleotides is required to initiate strand displacement. Because a longer region will increase the rate of displacement, and it is generally desirable in the assay to reduce the rate of displacement, so as to facilitate measurement, this length of 4–20 nucleotides is generally preferred. A length of 5–7 nucleotides is particularly preferred.

Figure 10:
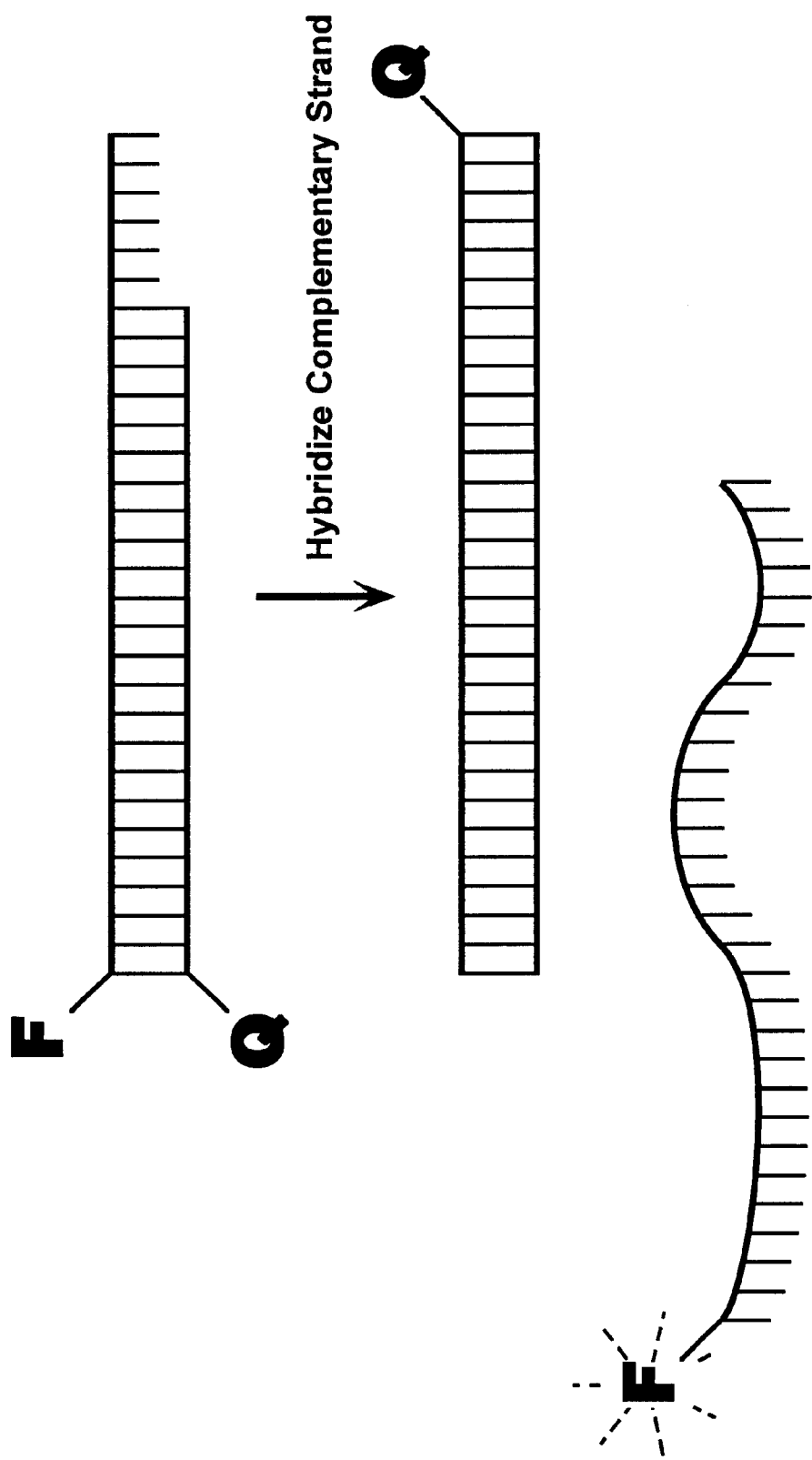
FIG. 10 is a schematic illustrating the displacement of a shorter, quenching strand from an F/Q indicator duplex by a longer, nonquenching strand, in a kinetic displacement assay.

The first and second strands are allowed to form a duplex in the absence of the ligand. In the present example, the "F" and "Q" groups are thus in proximity, giving a minimum level (when Q is a quenching group) of fluorescence. The displacing strand is added, and the rate of displacement, as indicated by an increase (or other change) in fluorescence over time, is observed (see FIG. 10). The experiment is then repeated in the presence of increasing amounts of ligand. A strongly binding ligand will stabilize the initial duplex and thus slow the rate of displacement. It is also expected that a ligand binding closer to the overhang site will also have a greater effect on inhibiting displacement.

In a variation on this assay, an array of different RNA pairs is exposed to the test ligand, and then to a ds-RNA binding protein. In this case, the sequences which do not strongly bind the test ligand will have a more extensive protein coating, and thus will be less susceptible to displacement by a displacing RNA strand.

Figure 11:
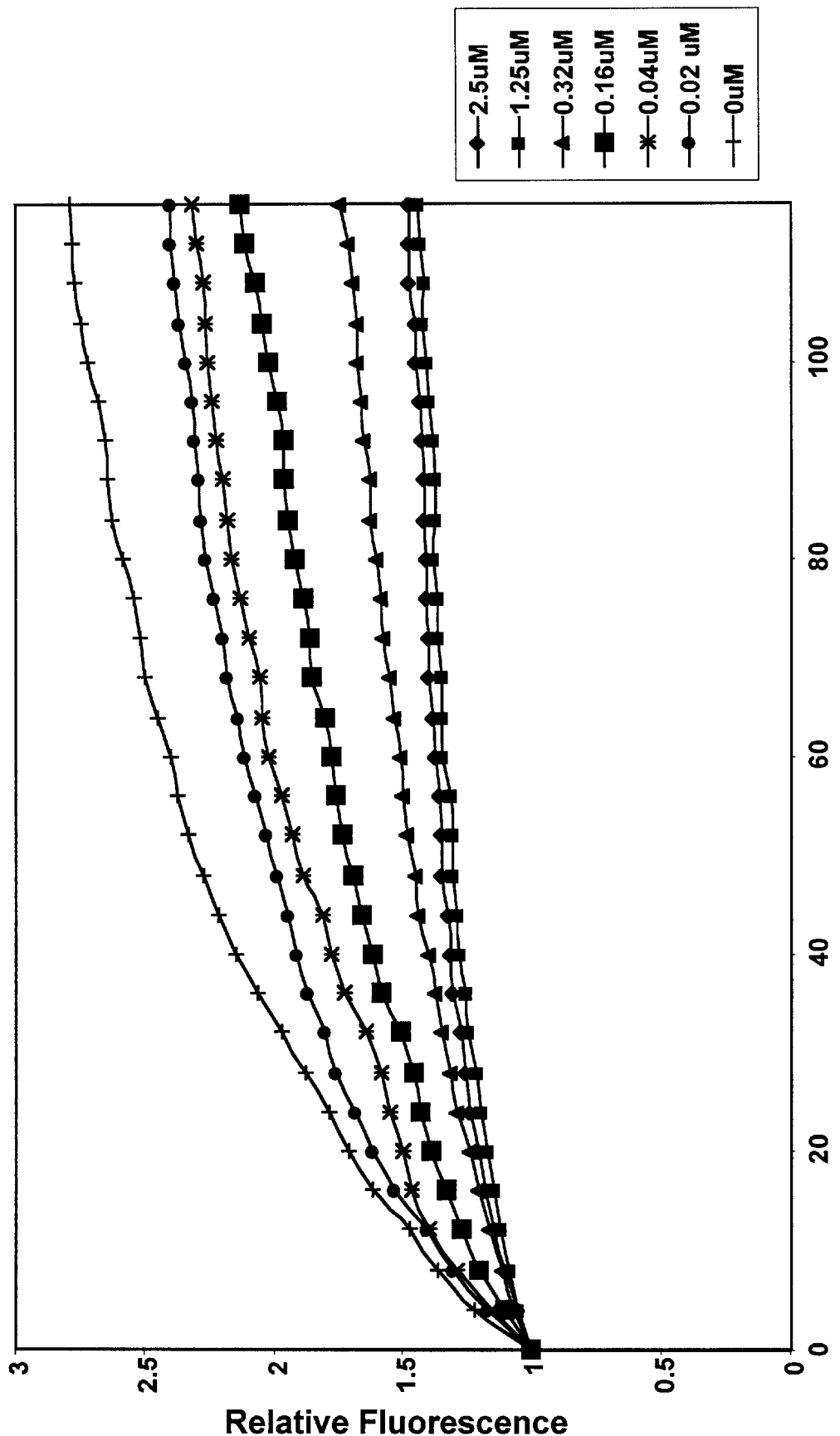
FIG. 11 shows the change in fluorescence in a kinetic strand displacement assay, in the absence of netropsin and in the presence of increasing amounts of netropsin.

Results of a fluorescence quenching strand displacement assay are given in FIG. 11. An F/Q indicator duplex of oligonucleotides having SEQ ID NO: 75 and SEQ ID NO: 76, as shown in Table VI, is formed in the absence of drug (0 $\mu$M curve) and in the presence of increasing amounts of netropsin (remaining curves). The displacing strand, having SEQ ID NO: 77 (Table VI), is added, and the increase in fluorescence is observed over time. As shown in FIG. 11, fluorescence increased about 175% in 2 hrs in the absence of drug, as the shorter strand (SEQ ID NO: 76) was displaced. About 0.08 $\mu$M drug was effective to detectably slow the rate of displacement, and at 1.25–2.5 $\mu$M, the increase at 2 hrs was reduced to about 40%.

TABLE VI

Oligos used in Kinetic Strand Displacement Assay

| Seq. ID No. | Sequence |
| --- | --- |
| | Strand Displacement Oligos |
| 75 | 5'-F-CAACGATAGCCGATGTTAGGCAGCTCAG-3' |
| 76 | 3'-Q-GTTGCTATCGGCTACAATCCG-5' |
| 77 | 3'-GTTGCTATCGGCTACAATCCGTCGAGTG-5' |
| | Duplex Competition Oligos |
| 78 | 5'-CAAAAATTTTTC-3' |
| complement | 3'-GTTTTTAAAAAG-5' |
| 79 | 5'-CCCGCGCGCGCC-3' |
| | 3'-GGGCGCGCGCGG-5' |
| 45 | 5'-GGAAGGAAGGAA-3' |
| | 3'-CCTTCCTTCCTT-5' |

Figure 12:
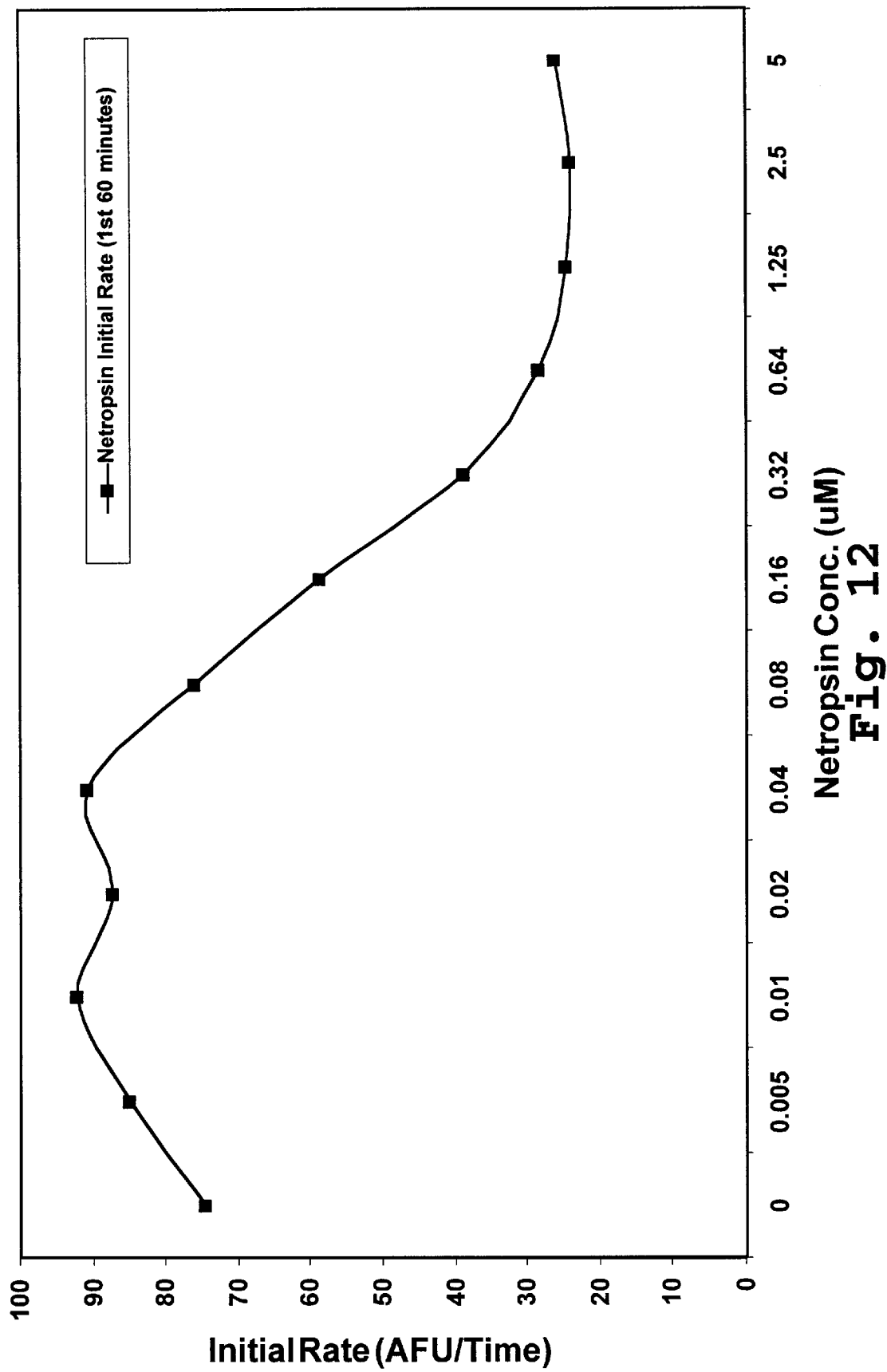
FIG. 12 shows how the initial rate of the displacement reaction of FIG. 11 varies in the presence of increasing amounts of netropsin.

FIG. 12 shows the change in the initial rate of displacement of the shorter oligo, derived from the data of FIG. 11, in the presence of increasing concentrations of netropsin. Again, a notable decrease in displacement is seen at about 0.08 $\mu$M of the drug.

Figure 13:
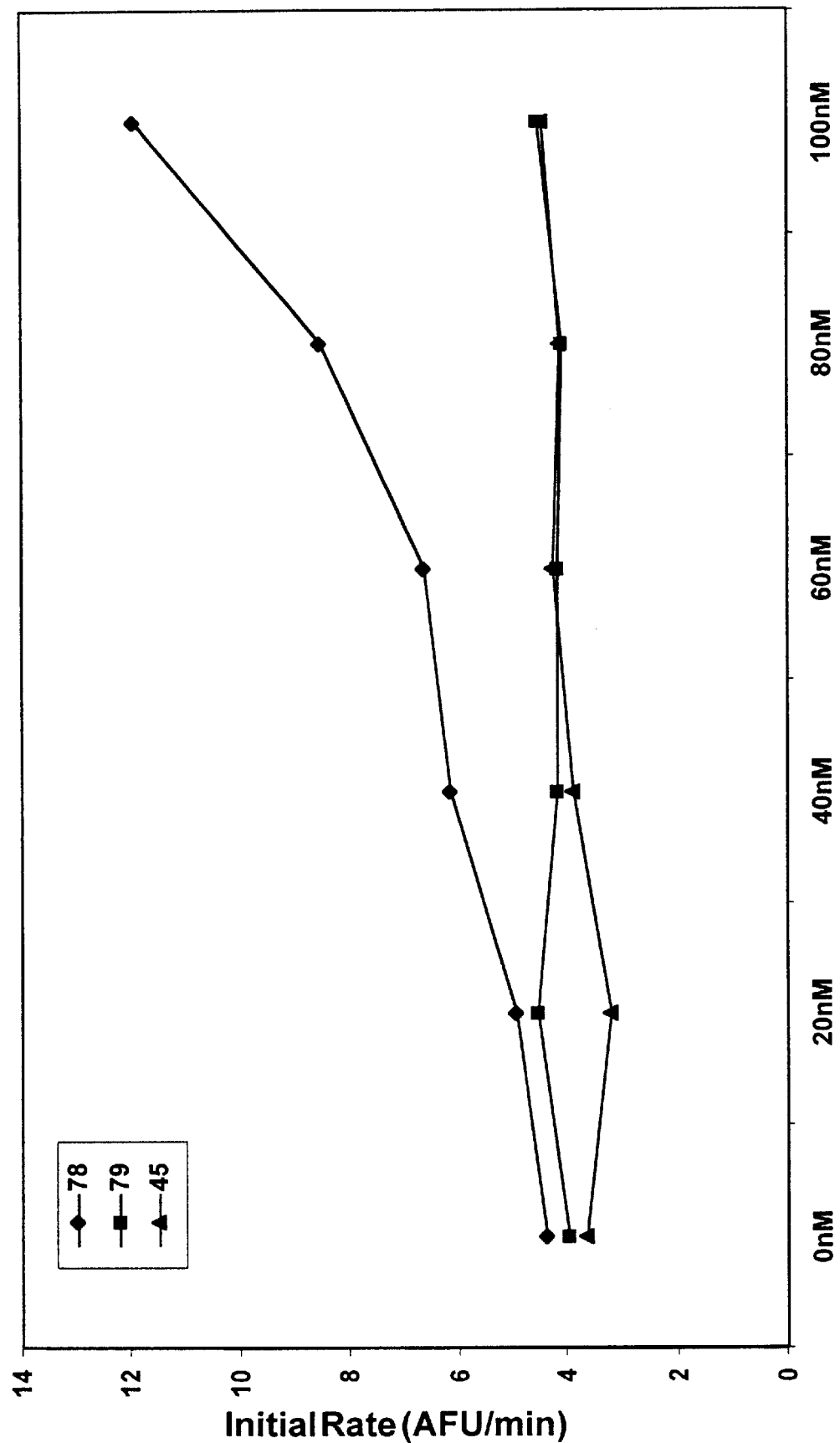
FIG. 13 shows the effect of specific, unlabeled DNA competitors (SEQ ID NO of top strand given in legend) on the initial rate of displacement in the system shown in FIG. 11.

Additional experiments were carried out in which specific, unlabeled DNA competitor duplexes, also shown in Table VI, were added to the assay. FIG. 13 shows the effect of these competitor duplexes on the rate of displacement. The SEQ ID NO of the top strand of each duplex is given in the Figure legend. Netropsin is believed to bind preferentially to A/T rich regions of DNA, as discussed above. It is expected, therefore, that the A/T rich oligonucleotide, having SEQ ID NO: 78, would competitively bind the drug, prevent it from binding to the indicator oligonucleotides, and thus counteract the effect of the drug in slowing the displacement reaction. Such an effect is shown in FIG. 13, where the rate of displacement is increased by increasing amounts of the A/T rich competitor duplex.

A disadvantage of the displacement assay as compared to the direct assay, above, is that the range of signal is typically narrower, and it tends to show less distinction between stronger and more weakly binding ligands. As noted above, however, the direct assay is best carried out under conditions at which the first and second strands exist in single stranded form in the absence of the ligand. The present assay however, begins with the first and second strands in duplex form, and does not require comparison of hybridized and fully denatured sequences. Accordingly, displacement assays using longer sequences may be carried out at lower temperatures than would generally be required in a direct assay. The displacement assay is thus useful for determining binding affinities of large ligands, such as proteins.

EXAMPLES

The following examples illustrate, but are not intended to limit the invention.

General Procedures

Direct Assays: Direct binding experiments were performed at room temperature (~25° C.) in the following buffer: 10 mM HEPES, pH 7.5, 0.1 mM EDTA, and 10 mM NaCl. Each assay was done in 200 µl volume in a black flat-bottom microtiter plate. The oligo concentrations in these experiments were 25 nM for fluorescein labeled oligo and 40 nM for the DabCyl™ labeled oligo. In some experiments, transfer RNA was added at concentrations of 10–50 µg/ml to weaken non-specific interactions between DNA binding drugs and the indicator oligos.

Competition Assays: Competition experiments were generally done in 10 nM HEPES, pH 7.5, 0.1 mM EDTA and 50 mM NaCl. The drug concentration used in the competition assays depends upon the affinity of the drug for a given indicator. For the competition experiments shown, the netropsin and distamycin concentrations used were 0.4 µM. The amount of competitor oligo used was varied from 0.2 µM to 1.0 µM. The data shown is from competition experiments using 0.4 µM unlabeled duplex competitors (see Tables II–V for the sequences of the competitor oligos).

Examples 1–2
Direct Binding Assays with Netropsin and Actinomycin

According to the general method described above, increasing amounts of netropsin or actinomycin, respectively, were added to mixtures of selected F/Q indicator oligonucleotide pairs, whose sequences are shown in the legends of FIGS. 1 and 2. The sequence of the "F" strand of each pair is given in the legends, along with single stranded controls, as indicated. The Figures show the level of fluorescence observed, relative to a control having no added drug, for each indicator pair (or single strand) as the level of added drug was increased. In these experiments, transfer RNA was added at concentrations of 10–50 µg/ml to weaken non-specific interactions between DNA binding drugs and the indicator oligos.

Example 3
Direct Binding Assay with Bekanomycin

According to the general method described above, increasing amounts of bekanomycin were added to mixtures of selected F/Q indicator oligonucleotide pairs, whose sequences are shown in the legend of FIG. 3. The Figure shows the level of fluorescence observed, relative to a control having no added drug, for each indicator pair (or single strand) as the level of added drug was increased.

Example 4
Direct Binding Assays with Netropsin

In this experiment, the assay was carried out in the same manner as Example 1, but in the absence of transfer RNA. The level of fluorescence observed, relative to control, with increasing amounts of drug is shown in FIG. 2D. The effect of non-specific binding, relative to FIG. 2A, can be seen at higher levels of added drug.

Examples 5–6
Competition Assays with Distamycin and Netropsin

According to the general procedure above, a mixture was formed of 0.4 µM drug and A/T rich F/Q indicator duplex (5'-CTTTATTATTTT-3'; SEQ ID NO: 2, and its complement). The assay employed 25 nM of the "F" sequence (SEQ ID NO: 2) and 40 nM of the complementary "Q" sequence. An unlabeled competitor duplex, selected from those whose sequences are given in Table II, was added at a 0.4 µM concentration, and the change in fluorescence was noted. Results for a series of competitor sequences are shown in FIG. 3.

Examples 7–8
Competition Assays with Distamycin and Netropsin: Poly-A and Poly-AT Sequences The assays described in Examples 5–6 were repeated, using unlabeled competitor duplexes with varying lengths of AA and A/T sequence motifs, whose sequences are given in Table III. Changes in fluorescence of the indicator duplex/drug mixtures on adding each competitor oligo are given in FIGS. 4 and 5.

Examples 9–10
Competition Assays with Distamycin and Netropsin: XAATTY Sequences The assays described in Examples 5–6 were repeated, using unlabeled competitor duplexes with all combinations of bases flanking an AATT site, whose sequences are given in Table IV. Changes in fluorescence of the indicator duplex/drug mixtures on adding each competitor oligo are given in FIGS. 7 and 8.

Example 11
Competition Assays with Netropsin: 5 bp Poly(AT) Sequences

The assays described in Examples 5–6 were repeated, using unlabeled competitor duplexes with all combinations of 5 bp A/T sequences, whose sequences are given in Table V. Changes in fluorescence of the indicator duplex/netropsin mixture on adding each competitor oligo are given in FIG. 9.

Example 12
Kinetic Strand Displacement Assay with Netropsin

A mixture was formed of 60 nM of a fluorescein labeled 28-nucleotide strand having SEQ ID NO: 75 (Table VI) and 90 nM of a Dabcyl™-labeled 21-nucleotide quenching strand (SEQ ID NO: 76) in a buffer containing 20 mM HEPES, pH 7.5, 0.1 mM EDTA, and 30 mM NaCl. The control experiment contained no added drug; for subsequent experiment, increasing amounts of netropsin were added. To start the displacement reaction, the displacing strand (SEQ ID NO: 77) was added at. concentrations of 35 nM to 60 nM. The fluorescence of the system was then monitored every 5 minutes for 90 to 120 minutes. Results for the control experiment and experiments containing 0.02 µM to 2.5 µM netropsin are shown in FIG. 11.

The initial rate of the displacement reaction was calculated from plots of fluorescence vs. time as the slope of the fluorescence curve from 0 to 60 minutes. This data is shown in FIG. 12.

Additional experiments were carried out in which specific, unlabeled DNA competitor duplexes, whose sequences are shown in Table VI, were added to the assay mixture. FIG. 13 shows the effect of these competitor strands on the rate of displacement, as determined by change in fluorescence of the system.

Example 13

Nucleic Acid Ligand Detection by SPA

Indicator oligonucleotides as shown in Table I are used in this assay. One strand of each duplex is labeled with biotin at either the 3' or 5'-end, and the complementary strand is labeled with a radioactive atom, such as $^3$H or $^{33}$P The two complementary strands are incubated with streptavidin-coated SPA beads (Amersham, Arlington Heights, Ill.) at room temperature in a buffer containing 20 mM HEPES, pH 7.5, 0.1 mM EDTA, and 20 mM NaCl. In the absence of ligand, and under these conditions, the oligonucleotides are in single-stranded conformation. As a result, the oligonucleotide containing the radioactive label is not in close proximity to the SPA bead, and the light given off by the beads is low, i.e., at background. Once a ligand that stabilizes the duplex conformation is added, the radioactive atom is brought into close proximity to the SPA bead, and the light emitted from the SPA bead increases.

The assay can be performed in commercially available high throughput screening systems, thus providing a high throughput method for finding novel nucleic acid binding compounds. In this system, a series of different oligonucleotide indicator pairs are placed in wells on a microtiter plate, and the assays are performed, using a series of candidate ligands. An exemplary assay utilizes an A/T rich DNA indicator oligonucleotide (CTTTATTATTTT; SEQ ID NO: 2), a G/C rich DNA indicator (CCGCGCC; SEQ ID NO: 6), a mixed sequence DNA indicator (GCGGTATTT; SEQ ID NO: 12), and an RNA indicator (CUAGAUCUGA; SEQ ID NO: 23), and the respective complements, in which one strand is biotinylated and the complementary strand is end-labelled with $^{33}$P. A ligand is titrated into wells containing each of the oligonucleotide indicator pairs, and the increase in light output is measured.

It is claimed:

1. A method of determining the relative binding affinities of a ligand, believed to exhibit preferential binding among different nucleic acid sequences, to different oligonucleotide sequences, comprising
   (i) forming a mixture of a first indicator pair of oligonucleotides comprising (a) a first oligonucleotide, which comprises a first group effective to produce a detectable signal, and (b) a second oligonucleotide, which is effective to hybridize with said first oligonucleotide by Watson-Crick base pairing, and which comprises a second group effective to detectably alter said signal when the first and second oligonucleotides hybridize to form a duplex;
   wherein said mixture is formed under conditions such that, in the absence of said ligand, said oligonucleotides exist primarily in single-stranded form;
   (ii) observing said signal from said mixture in the absence of said ligand;
   (iii) adding said ligand to said mixture;
   (iv) observing the effect of said adding on said signal;
   (v) comparing said effect with that observed upon carrying out steps (i)–(iv) with a second indicator pair of oligonucleotides; and
   (vi) determining the relative binding affinities of said ligand to said first and second indicator pairs by comparing said effects.

2. The method of claim 1, wherein said ligand is added in increasing concentrations, with said mixture held at a substantially constant temperature during said adding.

3. The method of claim 2, wherein said temperature is at or near room temperature.

4. The method of claim 1, wherein said second group is effective to stimulate or magnify said signal upon hybridization of the first and second oligonucleotides.

5. The method of claim 1, wherein said second group is effective to reduce or quench said signal upon hybridization of the first and second oligonucleotides.

6. The method of claim 1, wherein said signal is emitted radiation, and said second group is effective to alter the wavelength of said radiation, by absorption and reemission, upon hybridization of the first and second oligonucleotides.

7. The method of claim 1, wherein said first group is attached at the 5'-end or 3'-end of the first oligonucleotide, and said second group is attached at the 3'-end or 5'-end, respectively, of the second oligonucleotide.

8. The method of claim 1, wherein said first group is a radioactive emitting group, and said second group comprises a scintillant.

9. The method of claim 1, wherein said first group is a fluorescent group, and said second group is effective to absorb radiation emitted by said fluorescent group.

10. The method of claim 1, wherein said first group or said second group is a chemiluminescent group.

11. The method of claim 1, wherein said ligand is selected from a metal ion, a small organic molecule, a protein, and a multi-protein complex.

12. A method of determining the relative binding affinities of a ligand, believed to exhibit preferential binding among different nucleic acid sequences, to different oligonucleotide sequences, comprising (i) forming a mixture of a first indicator pair of oligonucleotides, comprising (a) a first oligonucleotide, which comprises a first group effective to produce a detectable signal, and (b) a second oligonucleotide, which is effective to hybridize with said first oligonucleotide by Watson-Crick base pairing, and which comprises a second group effective to detectably alter said signal when the first and second oligonucleotides hybridize to form a duplex; wherein said first and second oligonucleotides differ in length, such that said duplex has an overhang region, (ii) forming a duplex of said oligonucleotides, (iii) adding an unlabeled displacement strand which is effective to displace one of said oligonucleotides from said duplex in the absence of said ligand, thereby altering said signal, and (iv) observing said signal upon said adding, in the absence and in the presence of said ligand, (v) comparing the observed signals with those observed upon carrying out steps (i)–(iv) with a second indicator pair; and (vi) determining the relative binding affinities of said ligand to said first and second indicator pairs by comparing the observed signals.

13. The method of claim 12, wherein said forming, adding and observing steps are carried out at a substantially constant temperature.

14. The method of claim 13, wherein said temperature is: at or near room temperature.

15. The method of claim 14, wherein said overhang region is about 4–20 nucleotides in length.

16. The method of claim 12, further comprising the steps of (i) adding a competitor oligonucleotide, and (ii) observing the effect of such adding on said signal.

17. The method of claim 16, wherein said competitor oligonucleotide is selected from the group consisting of a duplex DNA, a duplex RNA, a duplex DNA/RNA hybrid, and a single stranded polynucleotide.

18. A method of determining the relative binding affinities of a ligand, believed to exhibit preferential binding among different nucleic acid sequences, to different oligonucleotide sequences, comprising (i) providing a first indicator pair of oligonucleotides, comprising (a) a first oligonucleotide, which comprises a first group effective to emit a detectable signal, and (b) a second oligonucleotide, which is effective to hybridize with said first oligonucleotide by Watson-Crick base pairing, and which comprises a second group effective to detectably alter said signal when the first and second oligonucleotides hybridize to form a duplex;

(ii) forming an indicator duplex of said first and second oligonucleotides, having bound thereto a ligand effective to stabilize said duplex;

(iii) adding a competitor oligonucleotide, (iv) observing the effect of such adding on the signal;

(v) comparing said effect with that observed upon carrying out steps (i)–(iv) with a second competitor oligonucleotide; and (vi) determining the relative binding affinities of said ligand to said first and second competitor oligonucleotides by comparing said effects.

19. The method of claim 18, wherein, in step (ii), said indicator duplex is formed under conditions such that, in the absence of said ligand, said first and second oligonucleotides would exist primarily in single-stranded form.

20. The method of claim 18, wherein said adding and observing steps are carried out at a substantially constant temperature.

21. The method of claim 20, wherein said temperature is at or near room temperature.

22. The method of claim 18, wherein said first group is attached at the 5'-end or 3'-end of the first oligonucleotide, and said second group is attached at the 3'-end or 5'-end, respectively, of the second oligonucleotide.

23. The method of claim 18, wherein said first group is a radioactive group, and said second group comprises a scintillant.

24. The method of claim 18, wherein said first group is a fluorescent group, and said second group is effect to absorb radiation emitted by said fluorescent group.

25. The method of claim 18, wherein said first group or said second group is a chemiluminescent group.

26. The method of claim 18, wherein said competitor oligonucleotide is unlabeled.

27. The method of claim 18, wherein said competitor oligonucleotide is selected from the group consisting of a duplex DNA, a duplex RNA, a duplex DNA/RNA hybrid, and a single stranded polynucleotide.

28. The method of claim 18, wherein said ligand is selected from a metal ion, a small organic molecule, a protein, and a multi-protein complex.

* * * * *